United States Patent
Eriksen et al.

(10) Patent No.: US 10,398,351 B1
(45) Date of Patent: Sep. 3, 2019

(54) SYSTEMS AND METHODS FOR MOTION COMPENSATION IN ULTRASONIC RESPIRATION MONITORING

(71) Applicant: RESPINOR AS, Oslo (NO)

(72) Inventors: Morten Eriksen, Oslo (NO); George Refseth, Oslo (NO); Knut Løklingholm, Oslo (NO); Nicolay Berard-Andersen, Olso (NO)

(73) Assignee: Respinor AS, Oslo (NO)

( * ) Notice: Subject to any disclaimer, the term of this patent is extended or adjusted under 35 U.S.C. 154(b) by 0 days.

(21) Appl. No.: 16/216,632

(22) Filed: Dec. 11, 2018

(51) Int. Cl.
*A61B 5/00* (2006.01)
*A61B 5/08* (2006.01)
*A61B 8/08* (2006.01)
*A61B 8/00* (2006.01)

(52) U.S. Cl.
CPC .............. *A61B 5/0816* (2013.01); *A61B 8/08* (2013.01); *A61B 8/4254* (2013.01); *A61B 2562/0219* (2013.01); *A61B 2562/0223* (2013.01)

(58) Field of Classification Search
CPC ....... A61B 5/0816; A61B 8/08; A61B 8/4254; A61B 2562/0219; A61B 2562/0223
See application file for complete search history.

(56) References Cited

U.S. PATENT DOCUMENTS

| | | | | |
|---|---|---|---|---|
| 6,321,109 B2* | 11/2001 | Ben-Haim | ........... | A61B 5/0422 600/424 |
| 6,332,089 B1* | 12/2001 | Acker | ................... | A61B 5/0422 128/899 |
| 2012/0209117 A1* | 8/2012 | Mozes | .................. | G06F 3/0325 600/439 |
| 2013/0165005 A1 | 7/2013 | Berard-Andersen et al. | | |
| 2014/0243671 A1* | 8/2014 | Holl | ..................... | A61B 8/4209 600/443 |
| 2018/0256075 A1 | 9/2018 | Souzy et al. | | |
| 2019/0090842 A1* | 3/2019 | Korukonda | .......... | A61B 8/4263 |

* cited by examiner

*Primary Examiner* — Michael T Rozanski
(74) *Attorney, Agent, or Firm* — Sterne, Kessler, Goldstein & Fox P.L.L.C.

(57) ABSTRACT

Described herein are example methods, devices and systems for motion compensation in ultrasonic respiration monitoring. A respiration detection system includes a first probe placed on a front side of a patient's body and a second probe placed on a dorsal side of the body. The first probe includes an ultrasound transducer, a first accelerometer unit and a magnetic field sensor unit, and the second probe includes a second accelerometer unit and magnetic field sensor unit. Due to respiration of the patient, the abdominal region of the body moves, creating measurement errors when an ultrasound beam is directed towards an internal structure (internal tissue region) inside the patient's body. Correction for such measurement errors uses input data from the first and second accelerometer units and the magnetic field sensor unit.

30 Claims, 13 Drawing Sheets

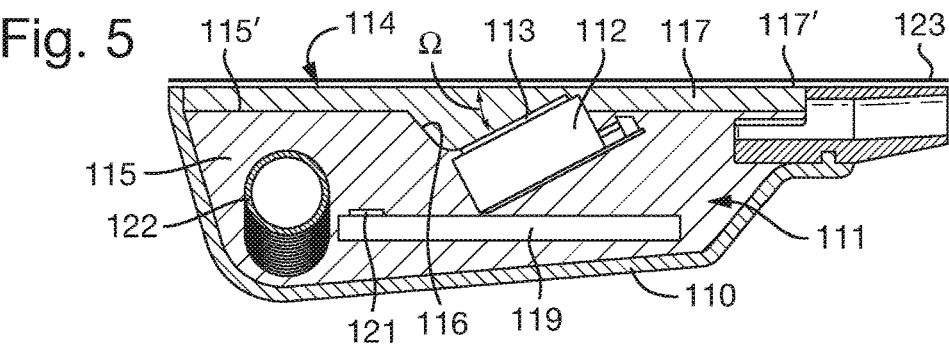
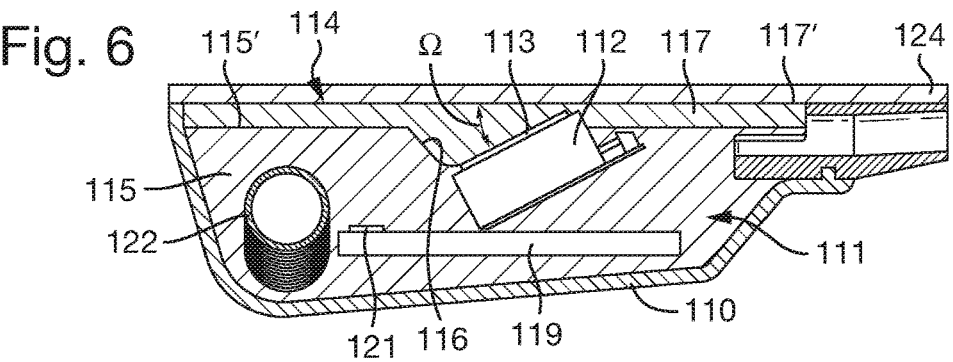
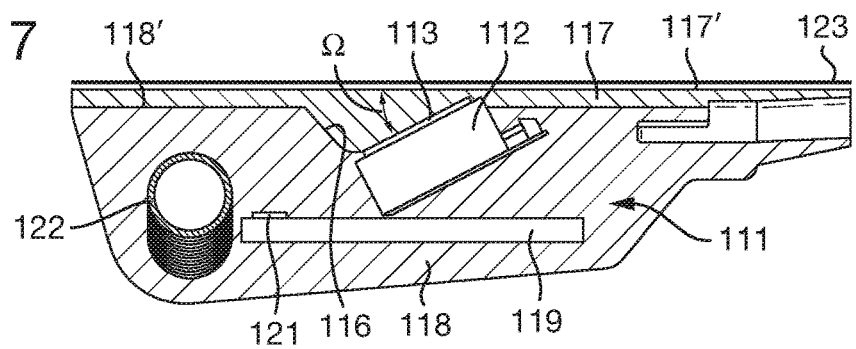
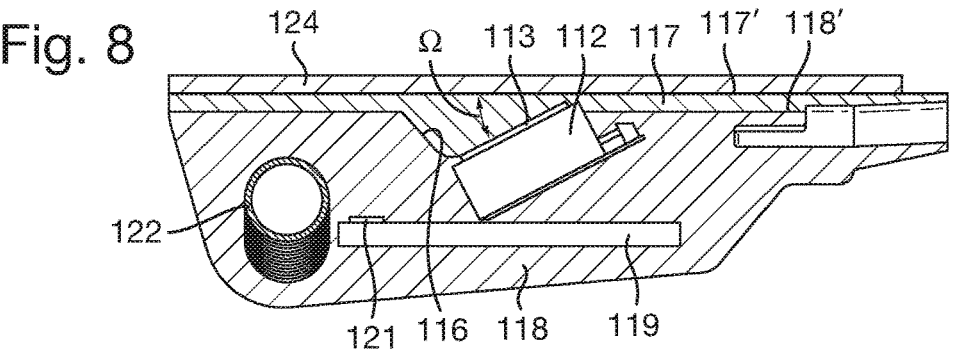

Cross Section Schematic

Motion During Inhalation

Effects of Abdominal Shape

The Doppler Echo Equation: $v = \dfrac{c \Delta f}{2 f_0 \cos(\alpha)}$

Rear (ancillary) Sensor Placement

The line connecting the electromagnet and the magnet pick-up should be perpendicular to the mattress.

SYSTEMS AND METHODS FOR MOTION COMPENSATION IN ULTRASONIC RESPIRATION MONITORING

CROSS-REFERENCE TO RELATED APPLICATIONS

This application is related to co-pending U.S. patent application Ser. No. 16/216,639, by Hamsund et al., entitled "Ultrasonic Transducer Device Probe for Respiration Monitoring," filed on even date herewith, which is incorporated herein by reference in its entirety.

BACKGROUND

Field

The present disclosure relates to methods, devices and systems for motion compensation in ultrasonic respiration monitoring of patients, including correcting for measurement errors resulting from movements of the abdominal region during respiration.

Background

Measurement and monitoring of respiration is important for treatment of a wide range of medical conditions in patients. The thoracic diaphragm is the main breathing muscle, and its dysfunction can be symptomatic of many respiratory disorders and conditions.

In order to monitor respiration, various ultrasonic transducer device probes have been utilized. For example, an ultrasonic transducer device may be located in a housing of a probe and embedded therein by an ultrasound sonolucent material, such as a silicone rubber material or another material that allows passage of ultrasonic waves. The ultrasonic transducer probe may be placed on the skin surface of a patient's body using a double-sided tacky tape having a reinforcing web between its two tacky layers.

While such probes may be useful in monitoring respiration properties of a patient, it is important to take into consideration correction of error signals caused by movement of the probe on the front surface of the patient during respiration. For example, the abdominal region of the body moves as the patient breathes, which causes the probe to move. In some cases, the magnitude of such error signals may be significant to measurement reliability.

SUMMARY

The present disclosure relates to systems and methods for correcting measurement errors during ultrasonic respiration monitoring, in which the measurement errors result from abdominal movements in a patient's body during breathing. Embodiments of the invention detect motion of various tissues and structures in the body including, for example, the spleen, liver, or a kidney. But, for purposes of illustrating the principles of embodiment of the invention, the following discussions primarily focus on motion detection of the liver. For example, when comparing measurements made with an abdominal probe attached to the front side of the human body and moving with the abdominal wall, liver excursion appears to be about 30 to 40% less than when measuring with a mechanically fixed probe.

These measurement errors are caused by respiratory motion imposed onto the probe, counteracting the echo distance variations along the direction of the ultrasound beam. Such errors may present a risk to evaluation certainty of the respiration modes and parameters of patients, particularly for a patient with a respiration issue of medical concern. Thus, the aspects of the present disclosure relate to effectively compensating for such highly unwanted errors and providing higher accuracy in respiration monitoring.

In an embodiment, a respiration detection system includes a first probe and a second probe. The first probe is configured to be placed on a front side of the body of a patient, and the second probe is configured to be placed on a dorsal side of the body. The first probe includes an ultrasonic transducer, a first accelerometer unit, and a first magnetic field unit, in which the ultrasonic transducer, the first accelerometer unit, and the first magnetic field unit are stationary located in the first probe. The ultrasonic transducer is stationary located within the first probe and has a transceiving face oriented at an acute angle relative to a front plane of the first probe. The ultrasonic transducer is configured to produce an ultrasound beam at the transceiving face for transmission into an internal structure inside the body of the patient. The second probe includes a second accelerometer unit and a second magnetic field unit, in which the second accelerometer unit and the second magnetic field unit are stationary located in the second probe. The ultrasonic transducer, the first and second accelerometer units, and the first and second magnetic field units are coupled to a signal processor.

In another embodiment, a method for motion compensation in ultrasound-based detection of respiration parameters of a patient is disclosed. The method includes attaching a first probe to a front body surface of the patient, the first probe having an ultrasound transducer, a first accelerometer unit, and a first magnetic field unit, attaching a second probe to a dorsal body surface of the patient, the second probe having a second accelerometer unit, and a second magnetic field unit, and providing a signal processor coupled to the ultrasonic transducer, the first and second accelerometer units, and the first and second magnetic field units. The method further includes transmitting, from the ultrasound transducer in the first probe, an ultrasound beam into an internal structure inside the body of the patient, receiving, at the ultrasonic transducer in the first probe, ultrasound echo signals from the internal structure, generating, by the second magnetic field unit, a magnetic field transmitted to and detected by the first magnetic field unit, and calculating, using the signal processor, an orientation of the first accelerometer unit relative to a fixed coordinate frame using derived parameters from the first accelerometer unit, and further calculating the derived parameters as unit vectors representing an orientation of the ultrasound beam and an orientation of the first magnetic field unit. Additionally, the method includes calculating, using the signal processor, an orientation of the second accelerometer unit relative to a fixed coordinate frame using further derived parameters, and calculating the further derived parameters including body back support tilt angle (a) and unit vectors representative of a spatial direction from the second magnetic field unit to the first magnetic field unit, an orientation of the second magnetic field unit, and an expected direction of motion of the internal structure during exhalation, calculating, using the signal processor, any varying distance between the first and second magnetic field units based on the detection of the magnetic field, and processing, using the signal processor, results from the calculated orientations, derived parameters from the first and second accelerometer units, and the varying distance to generate correction parameters to compensate for measurement errors in received ultrasound echo signals.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 5 illustrates a cross-section of a first embodiment of the front ultrasonic transducer device probe, according to embodiments of the present disclosure.

FIG. 6 illustrates a cross-section of a second embodiment of the front ultrasonic transducer device probe, according to embodiments of the present disclosure.

FIG. 7 illustrates a cross-section of a third embodiment of the front ultrasonic transducer device probe, according to embodiments of the present disclosure.

FIG. 8 illustrates a cross-section of a fourth embodiment of the front ultrasonic transducer device probe, according to embodiments of the present disclosure.

Figure 1A:
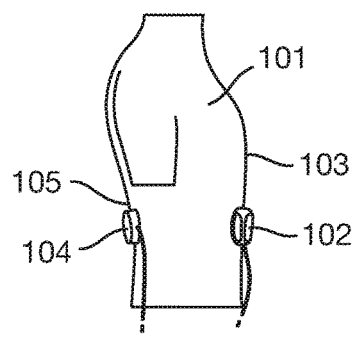
FIGS. 1A-1C illustrate example diagrams of a human torso showing ultrasonic transducer device placement, according to embodiments of the present disclosure.

Embodiments of the present invention will be described with reference to the accompanying drawings.

DETAILED DESCRIPTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment might not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. Further, any of the implementation variations may be carried out by a general purpose computer, as described below.

For purposes of this discussion, any reference to the term "module" or the term "unit" shall be understood to include at least one of software, firmware, or hardware (such as one or more of a circuit, microchip, and device, or any combination thereof), and any combination thereof. In addition, it will be understood that each module or unit may include one, or more than one, component within an actual device, and each component that forms a part of the described module may function either cooperatively or independently of any other component forming a part of the module. Conversely, multiple modules or units described herein may represent a single component within an actual device. Further, components within a module or unit may be in a single device or distributed among multiple devices in a wired or wireless manner.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

Figure 1B:
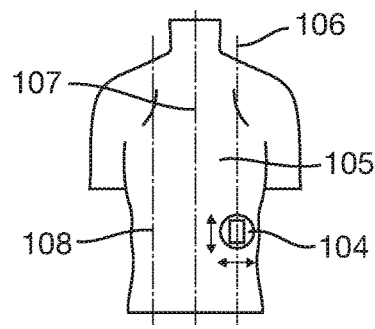
Figure 1C:
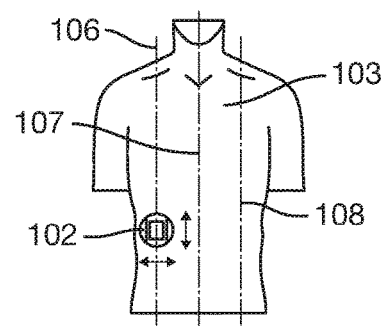

FIGS. 1A-1C illustrate example diagrams of a human torso showing ultrasonic transducer device placement, according to embodiments of the present disclosure. In particular, FIG. 1A shows a right side view of a torso 101 of a human onto which both an ultrasonic transducer device front probe 102 and a different rear probe 104 are attached to a front side 103 and dorsal side 105 of the human, respectively. FIG. 1B shows a tentative location of the rear probe 104, and FIG. 1C shows a tentative location of the front probe 102. In some embodiments, the front and rear probes may be referred to as first and second probes, respectively.

Although the probes 102, 104 are seen located close to the right mid-clavicular line 106, it will be appreciated that that these probes may be located laterally of the line 106 and/or at a different position along the direction of the line 106 than the positions shown in FIGS. 1B and 1C. The right mid-clavicular line is denoted as 106, and the left mid-clavicular line is denoted as 108. If an ultrasound beam is directed towards the spleen in the body, the probes are preferably located adjacent the line 108. If the ultrasound beam is directed towards a kidney, the probes are preferably located adjacent either line 106 or line 108, dependent on the selected one of the kidneys in the body.

It will be readily appreciated that measurement of motion of internal tissue region or internal structures is not limited to the liver. Any parenchymatous soft tissue that can be accessed by ultrasound from the body surface may be used. In addition to the liver, the spleen and the kidneys may be of particular interest for recording of diaphragm motion, according to some embodiments.

The present invention is described with reference to a currently preferred mode of detection involving detecting motion of the liver. This description is used for ease of explaining the structure, principles, and operation of the various embodiments of the invention and is intended to be exemplary rather than limiting.

Figure 2A:
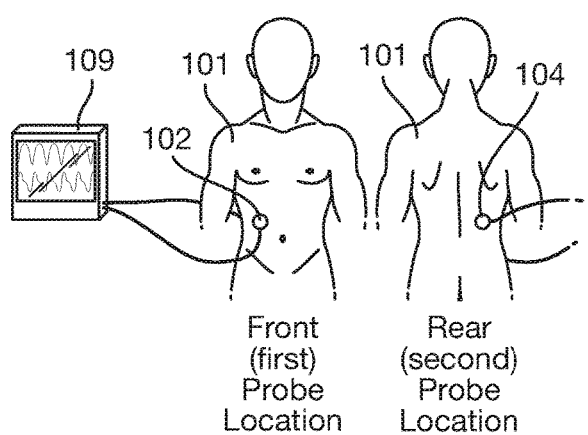
FIGS. 2A and 2B illustrate example diagrams of probe locations on the human body for motion detection of the liver, spleen, or kidney, according to embodiments of the present disclosure.
Figure 2B:
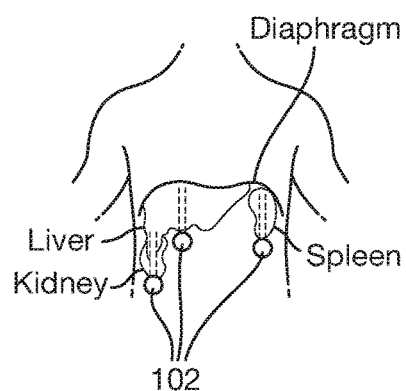

FIGS. 2A and 2B illustrate example diagrams of probe locations on the human body for motion detection of the liver, spleen, or kidney, according to embodiments of the present disclosure. Similarly to FIG. 1, FIG. 2A illustrates probe locations on the human body 101, in which the probes 102, 104 are suitably linked or coupled to a processor (e.g., signal processor 134 shown in FIG. 22) and display 109. FIG. 2B illustrates front probe 102 locations for motion detection of the liver, spleen, or kidney in a patient's body.

Figure 3:
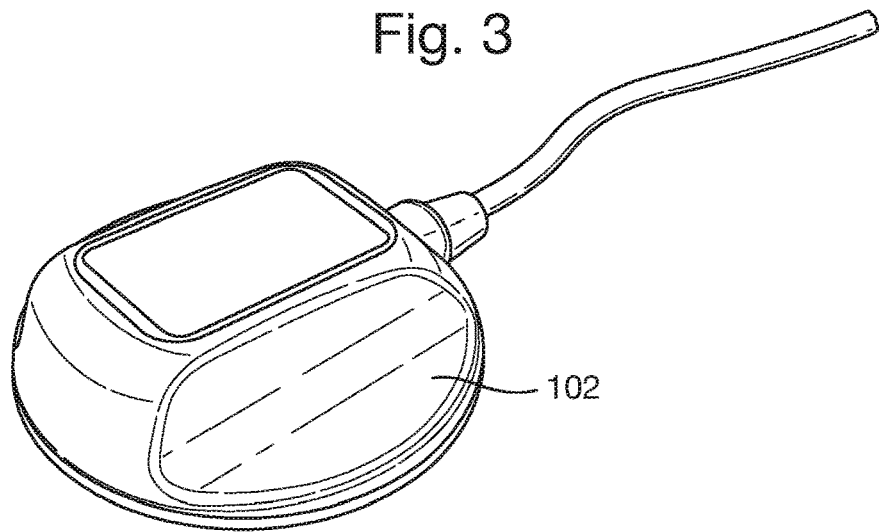
FIG. 3 illustrates a rear perspective view of a front ultrasonic transducer device probe, according to embodiments of the present disclosure.
Figure 4:
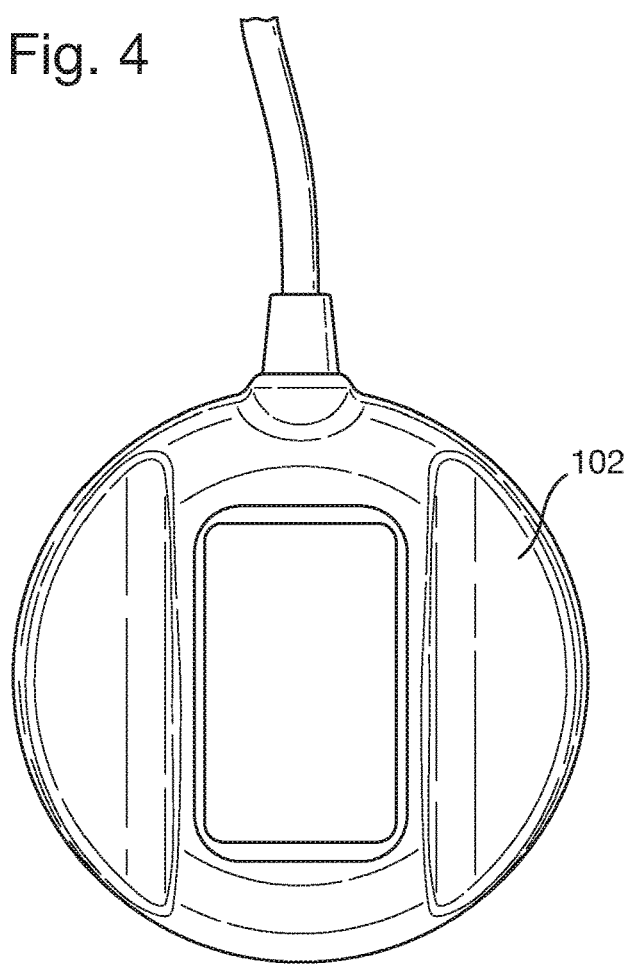
FIG. 4 illustrates a rear plan view of the probe of FIG. 3, according to embodiments of the present disclosure.

FIG. 3 illustrates a rear perspective view of a front ultrasonic transducer device probe 102, according to embodiments of the present disclosure. FIG. 4 illustrates a rear plan view of the probe 102 of FIG. 3, according to embodiments of the present disclosure.

The ultrasonic transducer device front probe 102 is further described with reference to FIGS. 5, 6, 9, and 10. The illustrated probe 102 is configured to be placed on a front body surface 103 of a human in order to direct an ultrasonic beam towards an internal structure and receive ultrasonic echo signals from the internal structure. The internal structure is at least one of the liver, the spleen, or a kidney of the human. In some embodiments, a tissue region may be referred to as an internal structure inside a patient's body.

The probe illustrated in FIGS. 5, 6, 9 and 10 has a housing 110, suitably made from a hard shell plastic material in a non-limiting example, with a cavity 111 in which an ultrasonic transducer 112 is located. A transceiving face 113 of the transducer 112 is oriented at an acute angle Ω relative to a front plane 114 of the housing at or adjacent a cavity mouth of the cavity of the housing. In some embodiments, the acute angle is suitably in a range of 0 to 60 degrees.

The transducer 112 is fixedly located in the cavity 111 of the housing 110 by means of at least a body 115 of first material comprising an ultrasound non-sonolucent material which extends towards the front plane 114. It will be observable that the body 115 of the first material surrounds a recess 116 extending from the transceiving face 113 towards the front plane 114.

A first part of a body 117 of a second material comprising an ultrasound sonolucent material is located in the recess 116 at and in front of the transceiving face 113 of the transducer towards the front plane 114. A second part of the body 117 of the second material is in addition applied onto a front surface 115' of the body of the first material and made integrally engaged therewith. In some embodiments, the first and second parts of the body 117 are integral.

FIGS. 7, 8, 11 and 12 illustrate additional embodiments of the front ultrasonic transducer device probe. In particular, there is no shell housing 110 and housing cavity 111 present in the embodiments of FIGS. 7, 8, 11 and 12, which differ from the embodiments of FIGS. 5, 6, 9 and 10. Instead, in the embodiments of FIGS. 7, 8, 11 and 12, the housing is simply constituted or formed by a body 118 of a first material, suitably of the same type of material as that of the body 115.

As shown in the embodiments of FIGS. 9-12, it is noted that the transducer 112 is supported in a different way than that in the embodiments of FIGS. 5-8. For example, in FIGS. 5-8, the transducer 112 is supported by a printed circuit board 119 and the body 115. In FIGS. 9-12, the recess is lined with an open-ended socket-like member 120 of ultrasound non-sonolucent material, and the transducer 112 is mounted at a bottom region of the open-ended socket-like member 120. The material of the member 120 exhibits an acoustic dampening property, and an outer wall of the member 120 is configured to engage the body 115, 118 of the first material. In FIGS. 9-12, transducer 112 and the open-ended socket-like member 120 extend from a printed circuit board 119. The member 120 with the transducer 112 located therein, as well as the printed circuit board, are supported by and embedded in the body 115, 118 of the first material.

Figure 22:
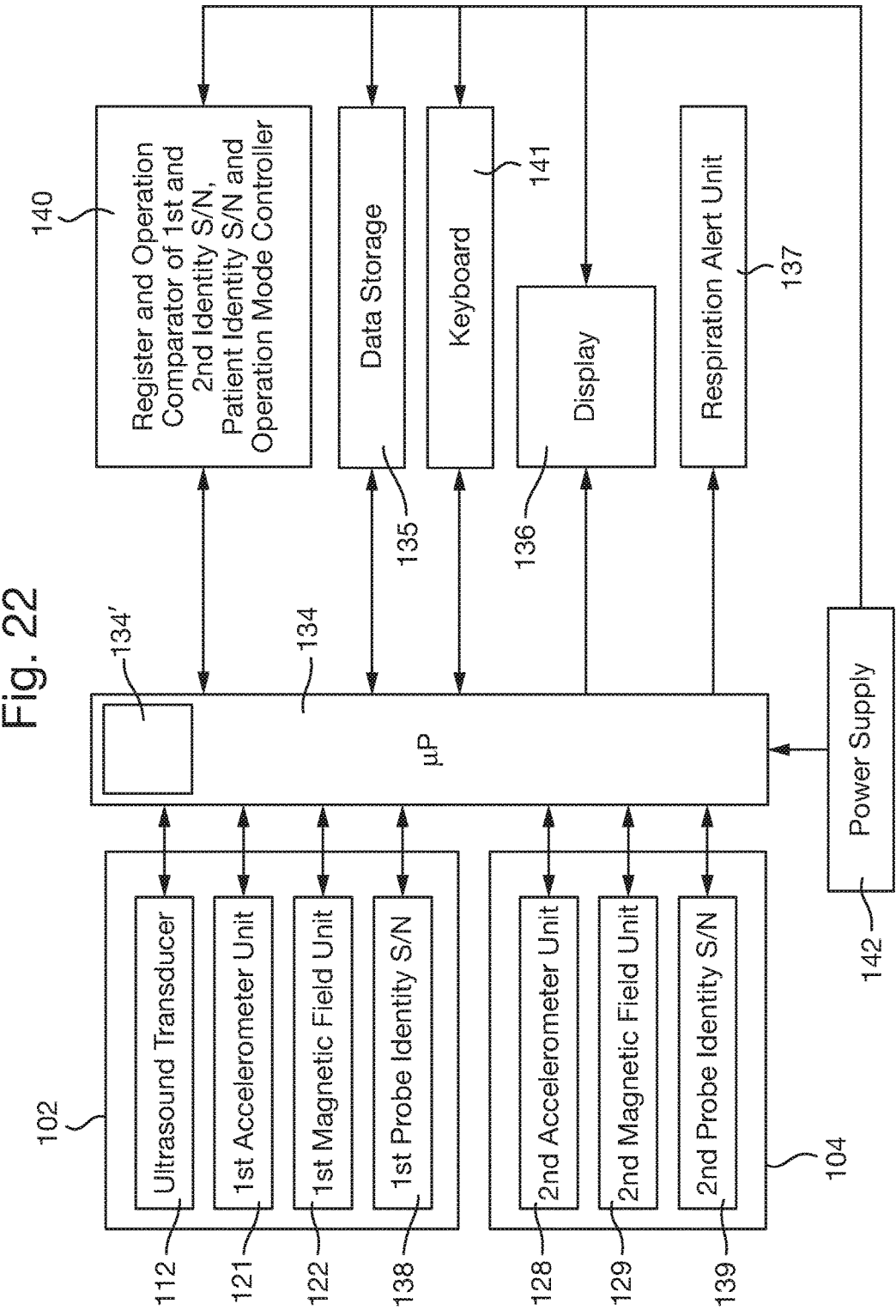
FIG. 22 illustrates a simplified block schematic diagram of an embodiment of the inventive system for performing signal processing related to range calculation and motion compensation, according to embodiments of the present disclosure.

The probe 102 also contains an accelerometer unit 121 (shown schematically) and a magnetic field detection unit 122 which are embedded (e.g., encapsulated) in the body 115, 118 of the first material. The accelerometer unit 121, the magnetic field detection unit 122, and the transducer 112 are connected or coupled to the printed circuit board 119 and to a signal processor 134 (as shown in FIG. 22). The signal processor is further described below with respect to FIG. 22.

The housing 110 having the cavity 111 and the body 115 of first material are suitably composed of materials having compatible properties, in particular to bond well together, but suitably also to have e.g. similar thermal expansion properties. For example, materials for the housing 110 may include a suitable plastics material or polymer(s) and/or body 115 of the first material may include an ultrasound non-sonolucent silicone rubber material or the like. In order to make a silicone rubber material ultrasound non-sonolucent, a variety of possible additives are available (e.g., calcium carbonate, titanium dioxide, zinc oxide, quartz, glass, or other additives). An example of silicone rubber with an additive is ELASTOSIL® RT 602 A/B. In order to make a plastics material ultrasound non-sonolucent, same or similar additives may be used. Thus, if the socket-like member 120 is formed of plastics material, such additives may be used. In some cases, the acoustic dampening property of such additives in silicone rubber or plastics material may be dependent on particle size and particle mass density (e.g., preferably particle density being highly different from the density of silicone rubber of plastic, both being about 1,000 kg/m³).

According to the embodiments of FIGS. 5-8 (e.g., where no housing shell 110 is present), the body 118 of first material forming the probe housing has a rear surface region, (e.g., the surface region which does not face the skin of the human body), such as that visible in FIGS. 3 and 4. In some embodiments, the first material being present thereat preferably has a non-sticky surface property.

Figure 11:
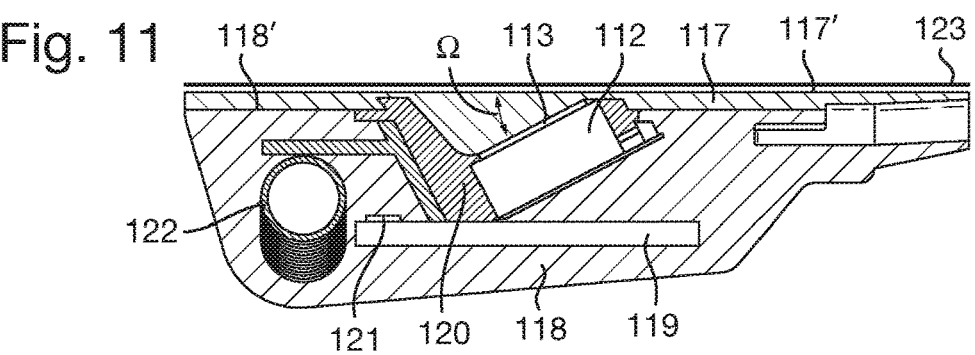
FIG. 11 illustrates a cross-section of a seventh embodiment of the front ultrasonic transducer device probe, according to embodiments of the present disclosure.
Figure 12:
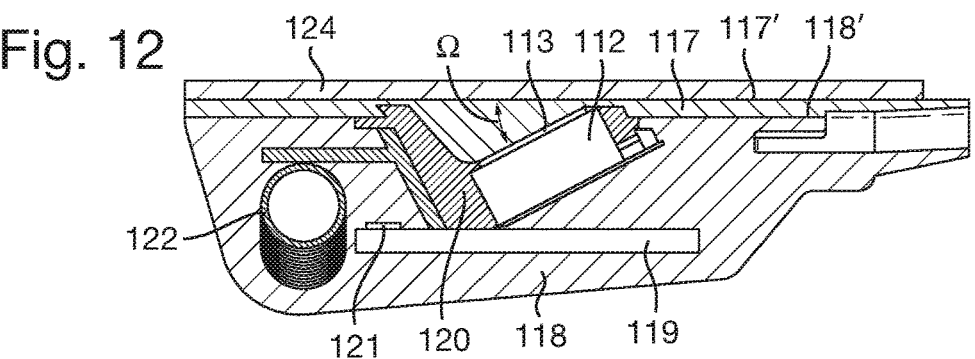
FIG. 12 illustrates a cross-section of an eight embodiment of the front ultrasonic transducer device probe, according to embodiments of the present disclosure.

It is noted that in the embodiments of FIGS. 7 and 8, the body 118 of a first material creates the recess 116, and in FIGS. 11 and 12, the body 118 surrounds the socket member 120 in which the transducer is located. The front surface 115', 118' of the body 115, 118 of the first material has the body 117 of the second material attached thereto. The front surface 117' of the body of the second material may exhibit one of: an inherent tacky property, an attachment face for an adhesive member or a double-sided tacky tape, and an engagement face for a tacky layer of a body of a third material.

If the front face 117' of the body 117 of the second material has a tacky surface property, the probe may be provided with a removable protective cover 123, the cover being removable prior to application of the probe onto the skin of the body 101. In this particular case, the probe is of a self-adhesive type suitably for single-use, although double sided tacky tape may be attached to the face 117' after a first use of the probe, provided that the face 117' is not contaminated in such a way that the tape will not adhere.

If the front face 117' is not to be used for adhering the probe 102 directly to the skin, then, as indicated by a general element 124, an adhesive member or the double-sided tacky tape is attached to the front face 117' of the body 117 of the second material. The adhesive member or double-sided tacky tape may be ultrasound sonolucent at least at a region faced by the transducer transceiving face 113. Additionally or alternatively, the general element 124 covering the front face 117' of the body 117 of the second material is the tacky layer of a body of a third material being ultrasound sonolucent.

The first and second materials are provided in the probe 102 as an integral structure, and both materials exhibit similar or compatible thermal and mechanical properties. Further, the second material and the third material are at least one of: identical, property compatible, and engagement compatible. The body material type of at least one of the first, second and third materials comprises a silicone rubber material. If the first and second materials are similar, the ultrasound non-sonolucent first material may have an added component thereto to effectively obtain its desired properties. For example, an additive, such as calcium carbonate, titanium dioxide, zinc oxide, quartz, glass, or the like, may be added to a silicone rubber material to make the silicone rubber material non-sonolucent. In an example embodiment, the first material is silicone rubber with one or more additives, whereas the second and third materials are silicone rubber. Many suitable silicone rubber materials are commercially available. For example, an ultrasound non-sonolucent silicone rubber material is ELASTOSIL® RT 602 A/B, and an ultrasound sonolucent material is ELASTOSIL® RT 601 A/B. In practice, it is important that additives do not interfere with the setting procedure of the silicone rubber and are biocompatible and exhibit excellent adherence to the silicone rubber material.

Figure 9:
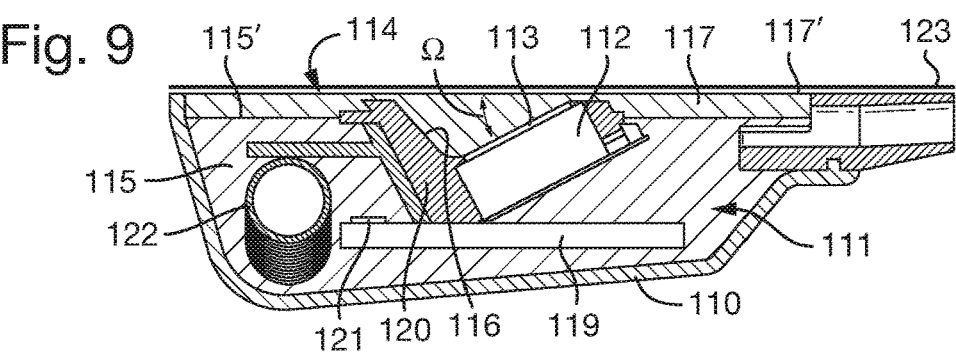
FIG. 9 illustrates a cross-section of a fifth embodiment of the front ultrasonic transducer device probe, according to embodiments of the present disclosure.
Figure 10:
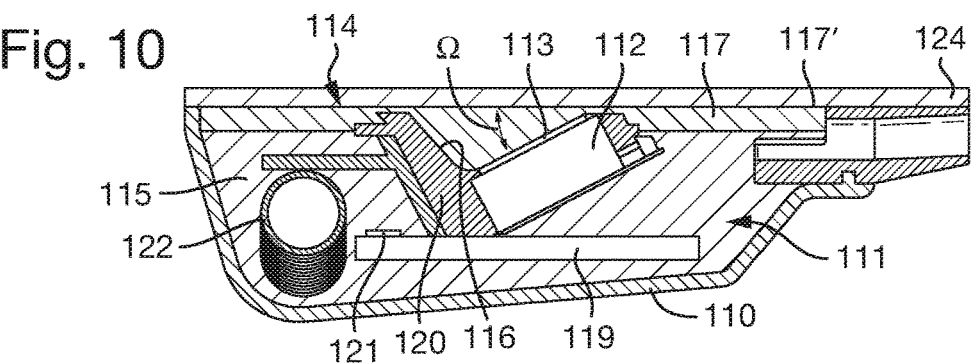
FIG. 10 illustrates a cross-section of a sixth embodiment of the front ultrasonic transducer device probe, according to embodiments of the present disclosure.
Figure 13:
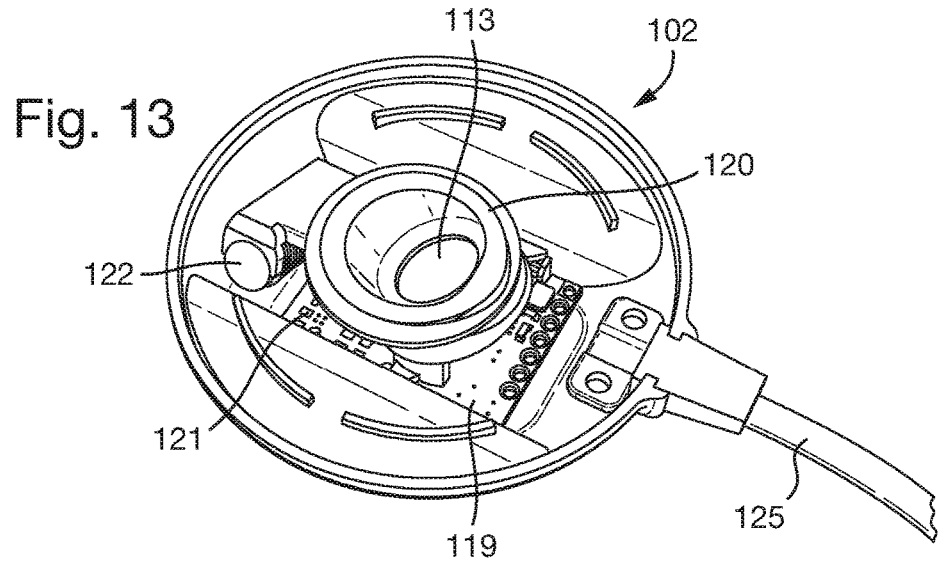
FIG. 13 illustrates a perspective, front full view of the probe of FIGS. 9 and 10, prior to installation of first and second materials in the probe, according to embodiments of the present disclosure.

FIG. 13 illustrates a perspective, front full view of the probe of FIGS. 9 and 10, prior to installation of first and second materials encapsulated in the probe, according to embodiments of the present disclosure. In particular, FIG. 13 shows the probe 102 prior to installation of an embedding (e.g., encapsulating) body 115 of a first material and application of a body 117 of a second material to fill the recess 116 down to the transducer transceiving face 113 and further to cover a front face 115' to the body 115 of the first material.

Figure 14:
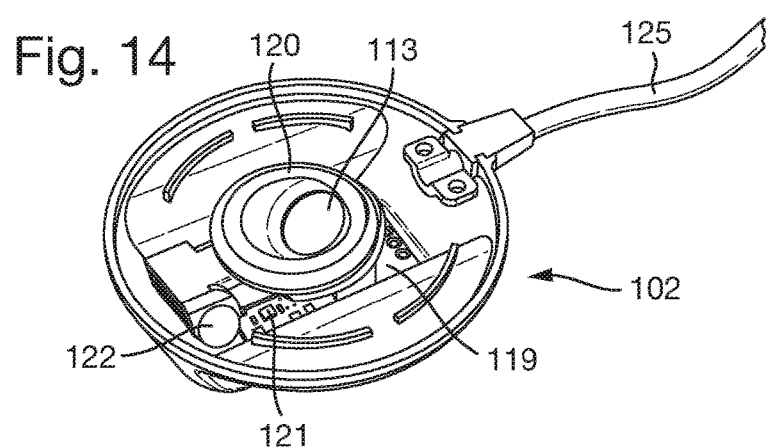
FIG. 14 illustrates another perspective, front full view of the probe of FIG. 13 from a different angle, according to embodiments of the present disclosure.
Figure 15:
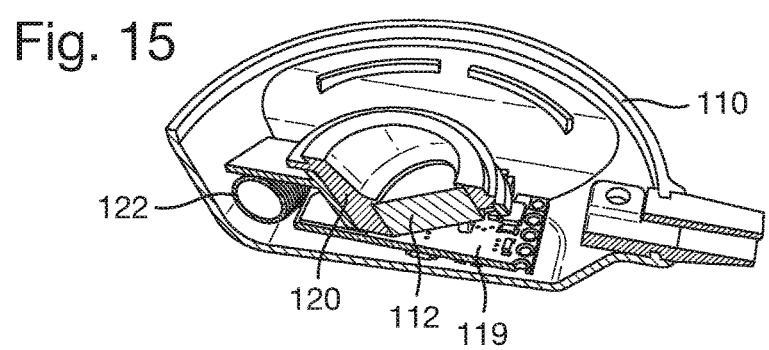
FIG. 15 illustrates a perspective, front sectioned view of the probe of FIGS. 13 and 14, according to embodiments of the present disclosure.
Figure 16:
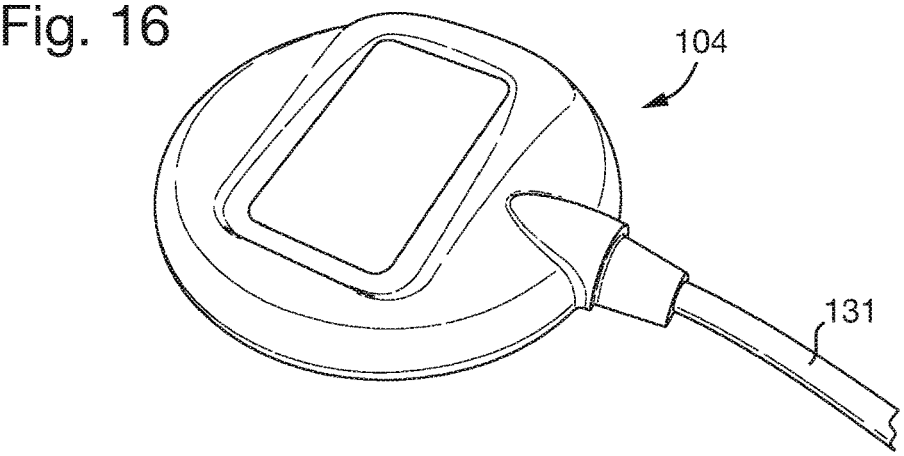
FIG. 16 illustrates a perspective rear view of a rear probe to be placed on the dorsal side of the human body and interface with the front probe on the front side of the human body, according to embodiments of the present disclosure.
Figure 17:
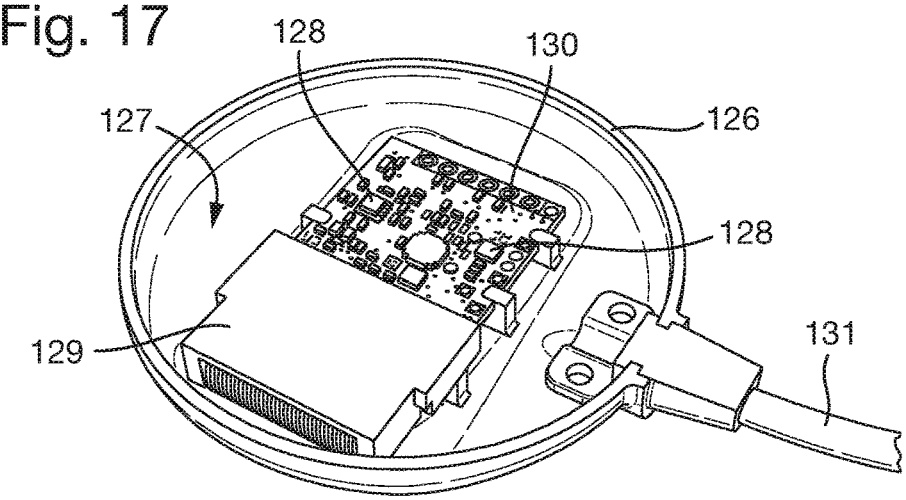
FIG. 17 illustrates a perspective, front full view of the probe of FIG. 16, prior to installation of a fourth material and optional application of a tacky body, according to embodiments of the present disclosure.
Figure 18:
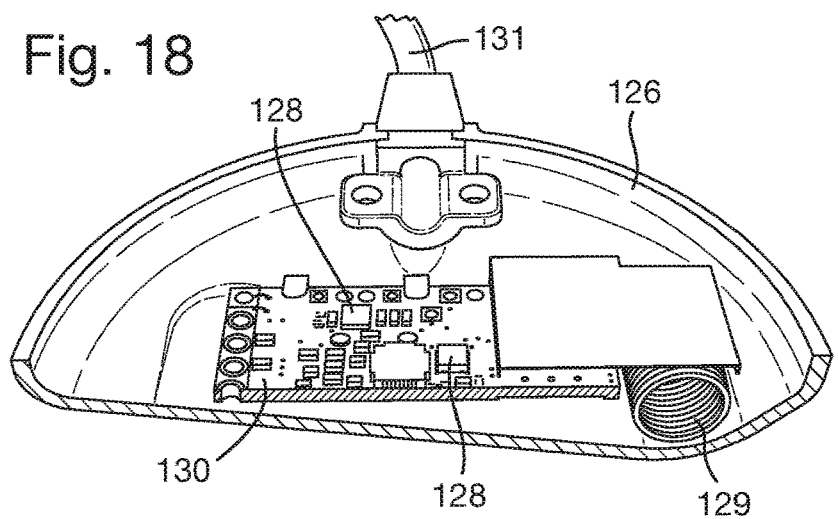
FIG. 18 illustrates a perspective, front sectioned view of the probe of FIG. 17, according to embodiments of the present disclosure.
Figure 19:
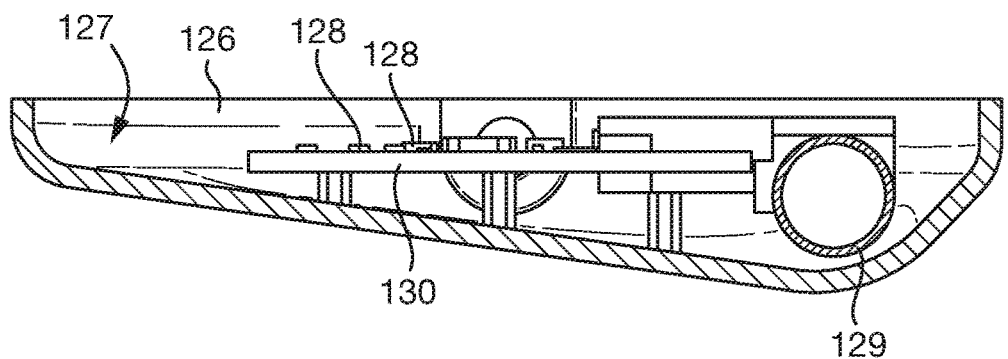
FIG. 19 illustrates a cross-section of the rear probe before installation of the fourth material, according to embodiments of the present disclosure.
Figure 20:
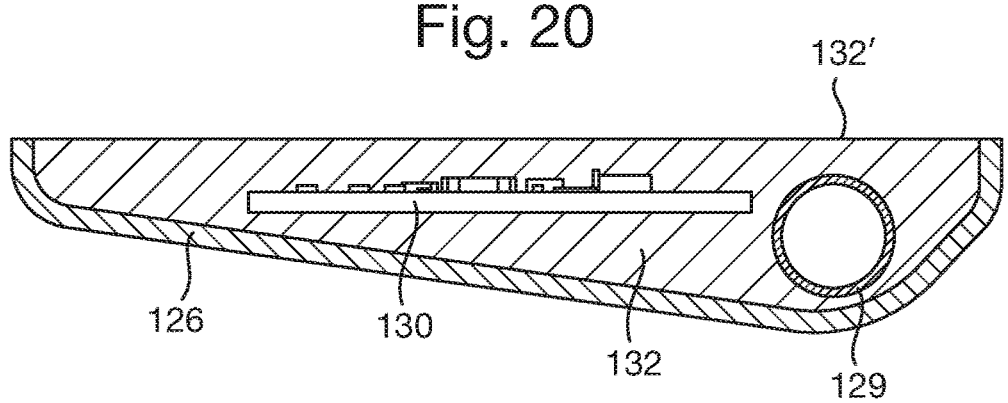
FIG. 20 illustrates a sectional view of FIG. 19 after installation of the fourth material, according to embodiments of the present disclosure.

FIG. 14 illustrates another perspective, front full view of the probe 102 as shown in FIG. 13, from a different angle, whereas FIG. 15 illustrates a perspective, front sectioned view of the probe 102 as shown in FIGS. 13 and 14, according to embodiments of the present disclosure. Wiring from a cable 125 onto the printed circuit board 119 has not been shown for sake of clarity. In some embodiments, cable 125 provides electrical connections between circuit board 119, processor, and display 109 (see FIG. 2A).

As discussed above, the first, front probe 102 is configured to cooperate or interface with a second, rear probe 104. These probes (shown in FIGS. 1A, 1B, 1C, 2A, and 2B are included in a respiration detection system configured to be located on a body surface of a human.

In the front probe 102, the ultrasonic transducer 112 is stationary located as described in reference to FIGS. 5-12 to produce an ultrasound beam directed outward from front surface plane 114 and towards an internal structure or a tissue region inside the body. Further, the probe 102 incorporates the first accelerometer unit 121 and the first magnetic field unit 122.

The second, rear probe 104 is shown in further detail in FIGS. 16-21. The probe 104 has a housing 126 in the form of a shell member of a plastics material and with an associated cavity 127 in which a second accelerometer unit 128 and a second magnetic field unit 129 are stationary located and suitably connected to a common printed circuit board 130. Wires from a cable 131 connecting to the printed circuit board are not shown for sake of clarity. In some embodiments, cable 131 provides electrical connections between circuit board 130, processor, and display 109 (see FIG. 2A).

The transducer 112, the first and second accelerometer units 121, 128, and the first and second magnetic field units 122, 129 are linked to the signal processor 134, as will be further described with reference to FIG. 22. The second accelerometer unit 128 provides for measurement of tilt angles of a surface supporting the dorsal side of the human body. The magnetic field sensor device of the first magnetic field unit 122 is a magnetic pickup coil in the illustrated embodiment. In an embodiment, the first and second accelerometer units 121, 128 exhibit at least two accelerometers each. In an embodiment, the first accelerometer unit 121 includes a three-axis accelerometer device.

Output signals provided to the signal processor 134 from the first and second accelerometer units 121, 128 and by use of the first and second magnetic field units 122, 129 are a function of spatial positional movements and orientation of the first probe 102 attached to the front side of the patient during respiration. The spatial positional movement and orientation is related to at least one of heave, roll, pitch and yaw type movements resulting from breathing by the patient.

The second accelerometer unit 128 and the second magnetic field unit 129 are stationary located in the cavity 127 of second housing 126 by means of a body 132 of a fourth material.

Figure 21:
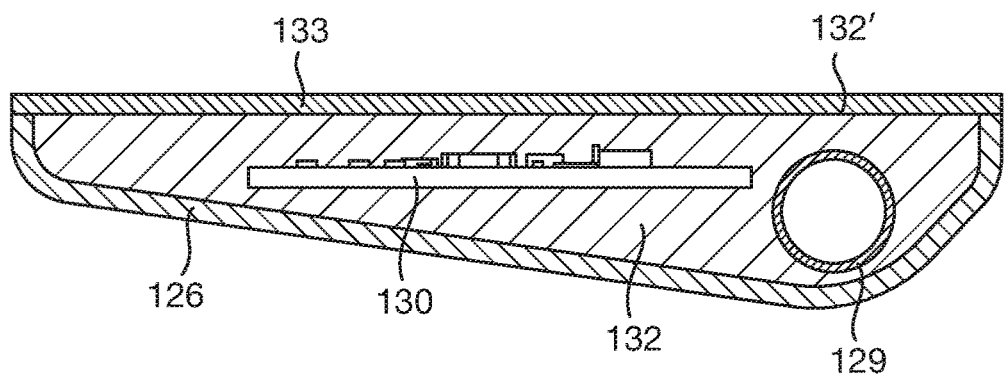
FIG. 21 illustrates a sectional view of FIG. 20 after addition of a tacky body of a fifth material, an adhesive member, or a double-sided tacky tape material, according to embodiments of the present disclosure.

A front face plane 132' of the body 132 of the fourth material provides one of: a tacky property, an attachment face for an adhesive member or a double-sided tacky tape, and an engagement face for a tacky layer of a body of a fifth material. In FIG. 21, at least one of the adhesive member, a double-sided tacky tape, and an engagement face for a tacky layer of a body of a fifth material is generally denoted by reference numeral 133.

At least one of the first, second, third, fourth, and fifth materials is suitably of a silicone rubber type. In order to avoid possible skin sores on the dorsal side of the body, at least a surface area of the second probe to abut or contact a dorsal skin area of the human body exhibits a biocompatible material, the abutting surface area of the second probe (e.g., the area of the probe surface in contact with skin) suitably being in the range of 5-100 cm$^2$. In the example embodiment described above, the first material is silicone rubber with an additive included to make the silicone rubber ultrasound non-sonolucent, and the second and third materials are ultrasound sonolucent silicone rubber. Continuing with the example embodiment, the fourth and fifth materials are silicone rubber. In some embodiments, the fourth and fifth materials might not need to take into consideration ultrasound aspects, because an ultrasound transducer might not be present in the dorsally located second probe 104. In additional embodiments, the first, second, third, fourth, and fifth materials are commercially available.

In some embodiments, the signal processor 134 (shown in FIG. 22) controls intensity, frequency and duration of magnetic field to be generated by the second magnetic field unit. The signal processor is configured to calculate, based on inputs from the first and second accelerometer units 121 and 128 and from the first magnetic field unit 122 interacting with the second magnetic field unit 129, movement and orientation of the abdominal wall of the patient's body in relation to direction of expected motion of the internal structure in question. The movement and orientation being related to respiration parameters associated with the abdominal muscles of the patient.

As described above, the internal structure or tissue region of the patient is at least one of the liver, spleen, or kidney of the patient. It will be readily appreciated that detected motion of the internal structure is a function of thoracic diaphragm movement in the patient's body.

As shown in FIG. 22, the processor 134 has associated therewith a data storage 135, to store respiration data of a patient during the course of monitoring, and a display 136 to observe visual representation of current or stored respiration data. The processor 134 also includes therein a transceiver section 134' operating with the transducer 112. In some embodiments, the processor 134 may cause a respiration alert unit 137 to generate one or more visual and/or audible alerts if one or more respiration parameters of the patient moves away from acceptable parameter ranges. Suitably, the front probe 102 has a first probe identity serial number device 138, and similarly the rear probe 104 has a second probe identity serial number device 139. These serial numbers 138, 139 are unique to the respective probes in use and might not be able to be changed.

Further, a registration and operation comparator unit 140 is provided and linked or coupled to the processor 134. In some embodiments, a patient's identity serial number (e.g., a social security, a tax personal code, or another identifier) may be entered into the unit 140 using a keyboard 141 which is linked to the processor 134, prior to and/or during use of the respiration detection system on a patient. In particular, with use on an infectious patient, it may be important that the front and rear probes 102, 104 when removed are not used on another patient. The unit 140 may therefore include an operation mode controller that prevents such second-hand use. In other cases, second-hand use may be acceptable if the probes 102, 104 are re-used on the original patient, and not on a new patient.

In some embodiments, reliability of a probe may deteriorate over time if the probes 102, 104 are re-used too many times. Thus, the operation mode controller may electronically limit numbers of re-use of a probe to a predefined number of uses, e.g., 3 to 10 uses, whereafter the processor 134 and the unit 140 may effectively block the serial numbers from the devices 138, 139. In other cases, the probes 102, 104 may have a respective self-tacky front face 117', 132', as typically could be used by an ICU (Intensive Care Unit) for single use. For these single-use probes, the probe identities may be blocked once the system is shut down, and the probes are removed from the patient. In some embodiments, a power supply 142 may deliver power to the processor 134, the data storage 135, the display 136, and the units 137, 140. In additional embodiments, required power to the probes 102, 104 are delivered via the processor 134.

Figure 27:
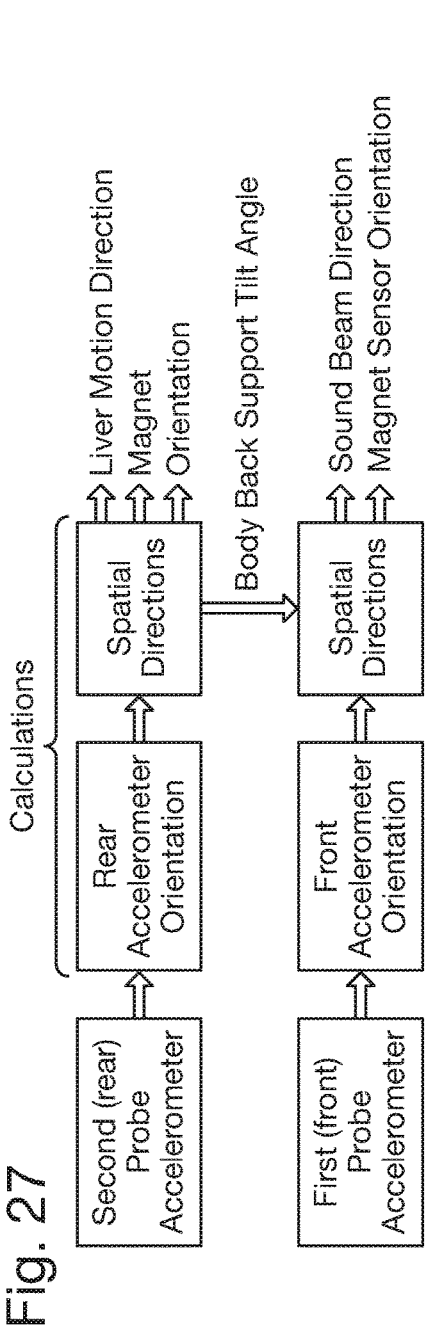
FIG. 27 illustrates a schematic diagram showing derivation of signals from accelerometers in the front and rear probes, according to embodiments of the present disclosure.
Figure 28:
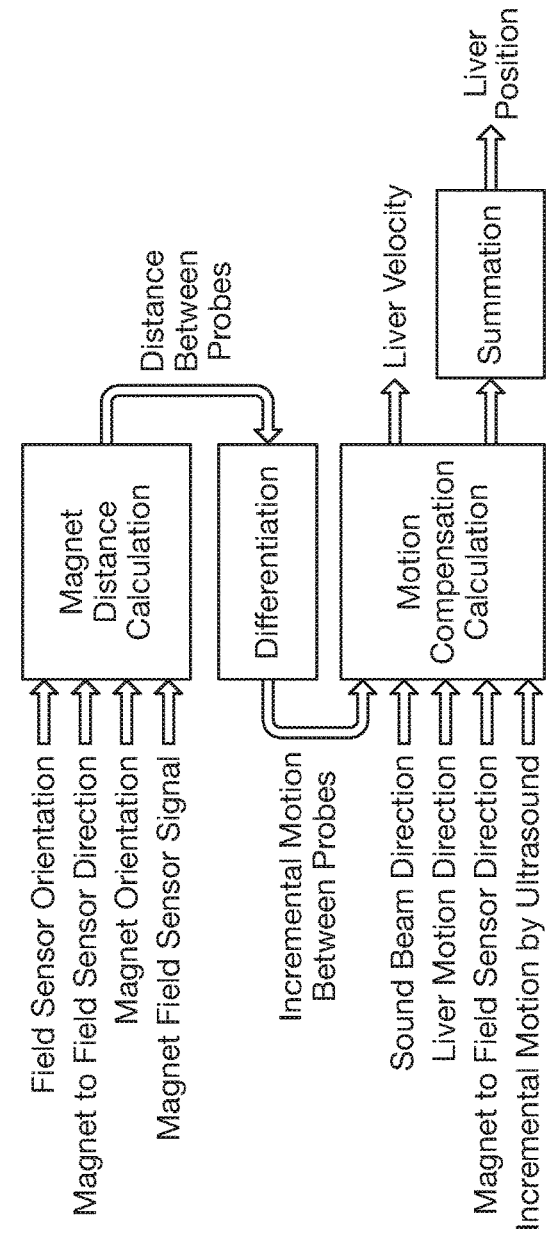
FIG. 28 illustrates a schematic diagram showing signal processing related to range calculation and motion compensation, according to embodiments of the present disclosure.

An example method for motion compensation of measurement errors during respiration monitoring is described herein with reference to FIGS. 23-26. In order to more easily appreciate the functions of the systems, reference is also made to FIG. 27, which schematically illustrates derivation of signals from accelerometers in the front and rear probes, and FIG. 28, which schematically illustrates signal processing related to range calculation and motion compensation, according to embodiments of the present disclosure.

The example method is used in ultrasound-based detection of respiration parameters of a patient. The detection uses an ultrasound beam 143 directed from and to an ultrasound transducer device 112 in a front probe 102 (located on a front side of the human body). The ultrasound beam 143 is directed from a front body surface of the human to an internal structure or a tissue region inside the body and is reflected back to the probe 102 as ultrasound echo signals.

In an embodiment, the method comprises:

(a) attaching a first probe 102 to a front body surface of the patient, the first probe 102 having the ultrasound transducer 112, the first accelerometer unit 121, and the first magnetic field unit 122, (b) attaching a second probe 104 to a dorsal body surface of the patient, the second probe 104 having the second accelerometer unit 128, and the second magnetic field unit 129, (c) providing the signal processor 134 coupled to the transducer 112, the first and second accelerometer units 121, 128, and the first and second magnetic field units 122, 129, (d) transmitting, from the ultrasound transducer 112 in the first probe 102, an ultrasound beam into an internal structure (or tissue region) inside the body of the patient, (e) receiving, at the ultrasonic transducer 112 in the first probe 102, ultrasound echo signals from the internal structure, (f) generating, by the second magnetic field unit 129, a magnetic field transmitted to and detected by the first magnetic field unit 122, (g) calculating, using the signal processor 134, the orientation of the first accelerometer unit 121 relative to a fixed coordinate frame using derived parameters from the unit 121, and further calculating derived parameters as unit vectors representing an orientation of the ultrasound beam 143 (see FIGS. 23-26) and an orientation of the first magnetic field unit, (h) calculating, using the signal processor 134, the orientation of the second accelerometer unit 128 relative to a fixed coordinate frame using derived parameters from the unit 128, and further calculating derived parameters including: body back support tilt angle (a) and unit vectors representative of a spatial direction from the second magnetic field unit 129 (e.g., an electromagnet) to the first magnetic field unit 122 (e.g., a sensor device located in the front probe 102), an orientation of the second magnetic field unit 129, and an expected direction of motion of the internal structure or tissue region (e.g., liver, spleen or kidney) during exhalation, (i) calculating in the signal processor 134 any varying distance between the first and second magnetic field units 122, 129 based on the detection of the magnetic field, and (j) processing, using the signal processor 134, the results from calculations in steps (g)-(i) to generate correction parameters to compensate for measurement errors in received ultrasound echo signals caused by abdominal wall movement due to respiration of the patient.

More specifically, the processing step (j) may comprise:

(k) decomposing a vector representing the distance between the first magnetic field unit 122 contained in the front probe 102 and the dorsally located second magnetic field unit 129 along the ultrasound beam direction 143, (l) differentiating the decomposed vector in time representing the distance to yield incremental motion values, (m) adding the incremental motion values in step (l) to incremental Doppler effect motion values as detected by use of ultrasound echo signals from the internal structure in at least a same time interval, (n) correcting the added motion values of step (m) for an instantaneous cosine value of an angle between the ultrasound beam 143 and direction of motion of the internal structure, and (o) summing the corrected and added motion values in order to obtain internal structure position variations describing corrected respiratory parameters.

The need for motion correction of the front probe will now be discussed in further detail below. Although the following discussion is primarily related to aspects of liver motion detection, it will be appreciated that embodiments of the disclosure may also be applied to motion detection of other tissues, such as the spleen or a kidney of the human.

During a pilot clinical study for evaluation of an ultrasound transducer device probe, it was observed that reproducibility of measurements provided by such an instrument was poor, and that re-positioning of the probe on the abdominal surface resulted in undesirable changes or deviations in the measured liver (and diaphragm) motion amplitudes. By analyzing possible causes for this, two factors were identified that might have contributed to the deviations.

Figure 23:
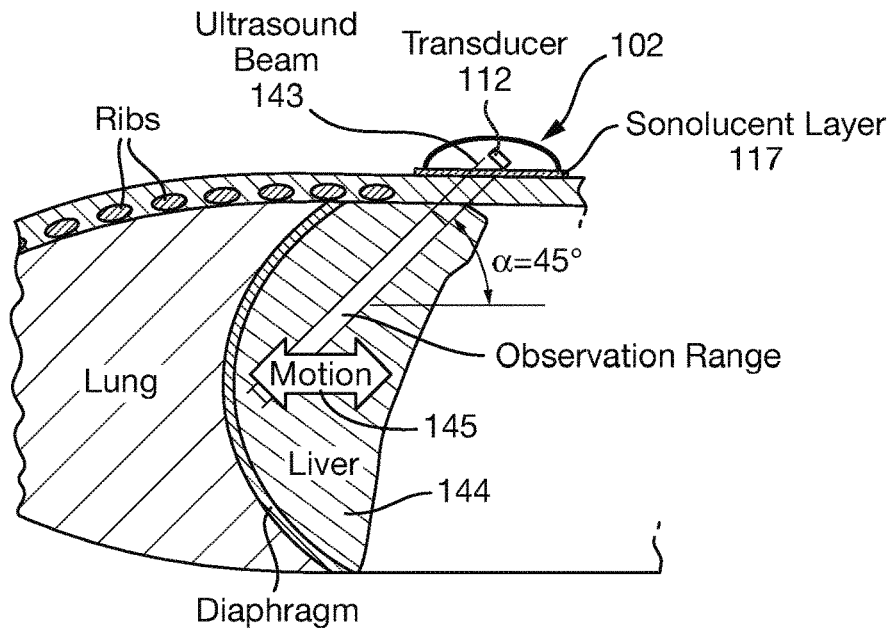
FIG. 23 illustrates a cross-section diagram showing basic principles for respiration detection using ultrasound beam directed at a human liver, according to embodiments of the present disclosure.
Figure 24:
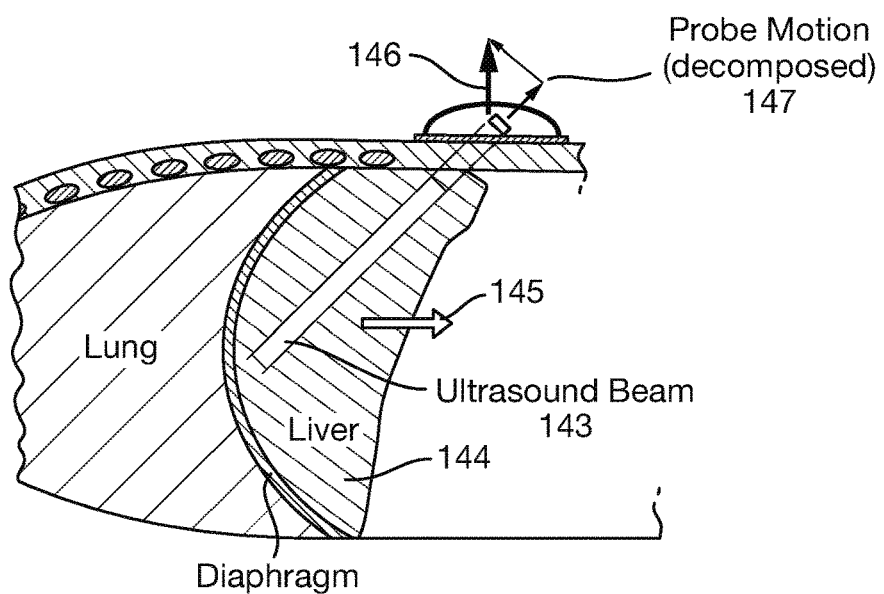
FIG. 24 illustrates a cross-section diagram showing motion of a chest and abdominal region of the human body during respiration, according to embodiments of the present disclosure.

First, the probe on the abdominal surface of a patient is moving up and down when the patient is breathing. This motion has a vector component along the ultrasound beam direction 143, and the motion of the probe gives a variable under-estimation of the true motion of the liver 144, as illustrated in FIGS. 23 and 24. When the liver 144 moves towards the probe 102 during inhalation, the probe will at the same time move away from the liver, and vice versa during exhalation. This occurrence was confirmed experimentally using a mechanically fixed probe that was not allowed to move, resulting in about 40% higher estimates of liver motion compared to a freely moving probe.

FIGS. 23 and 24 illustrate cross-section diagrams showing basic principles for respiration detection using ultrasound beam directed at a human liver and motion of a chest and abdominal region of the human body during respiration, according to embodiments of the present disclosure. In particular, the cross-section diagrams of FIGS. 23 and 24 show the motion 145 of the liver 144 and the motion 146 of the probe, and how the motion of the probe can be considered as having two components. One component 147 is along the ultrasound beam direction 143. This component will directly affect and disturb the estimated motion of the liver 144.

Figure 25:
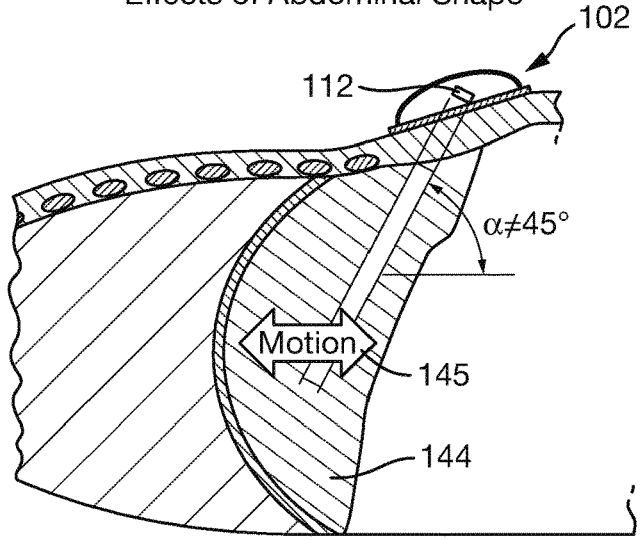
FIG. 25 illustrates a cross-section diagram showing effects of abdominal shape changes during respiration, according to embodiments of the present disclosure.

Second, the abdominal surface is conical, and not cylindrical. This abdominal shape will cause a variable tilt of the transducer 112 and the probe 102, and will thus affect the direction of the ultrasound beam 143. Just below the costal margin where the front probe 102 is placed in order to have acoustic access to the liver 144, there may be a substantial concavity of the surface in slim human subjects. And in obese human subjects, the surface is convex, as illustrated in FIG. 25. Thus, assumption of a fixed 45° angulation between the sound beam 143 and the direction 145 of the liver motion might not be valid.

Accordingly, embodiments of the present invention alleviate the issues discussed above.

Figure 26:
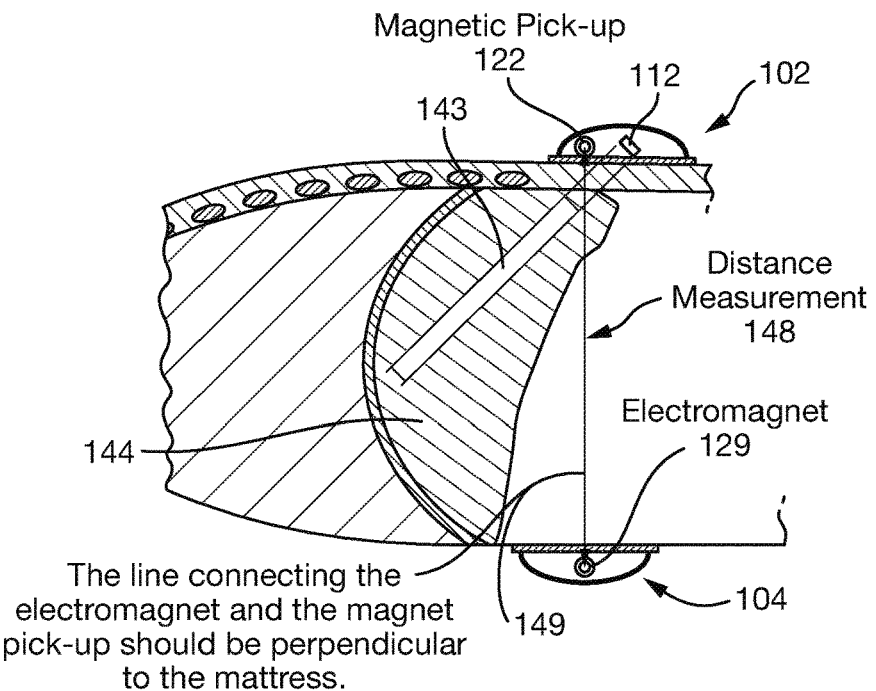
FIG. 26 illustrates a cross-section diagram showing rear (ancillary) sensor probe placement, as also shown in FIG. 1A, 1B, 2A, or 2B, according to embodiments of the present disclosure.

FIG. 26 illustrates a cross-section diagram showing the basic principle of distance measurement 148 through use of placement of a dorsal (ancillary) or rear sensor probe 104. In the non-limiting example, the human body is supine on a bed mattress (e.g., lying face upward).

The probe 102 is equipped with a 3-axis accelerometer module that uses the direction of the gravity vector to estimate tilt, allowing calculation of the actual spatial direction of the ultrasound beam relative to the motion of the liver.

In an embodiment, the extra, second (ancillary) sensor rear probe 104 is added at a location on the patient's dorsal side, vertically below the front probe 102 if the patient body is supine. If the patient is in an upright posture, the front and rear probes 102, 104 may be aligned, roughly at right angles to the spine direction of the human.

The rear, second sensor probe 104 contains the additional accelerometer unit 128 for measuring the tilt angle of a bed upon which the patient rests, since most ICU patients have an elevated bed. The tilt angle measurement may be utilized in order to have an estimate of the actual liver motion direction.

The rear sensor probe 104 also contains an electromagnet in the unit 129 that generates a weak alternating magnetic field that is sensed by a magnet pick-up coil in unit 122 of the front probe 102. The use of the electromagnet and magnet pick-up coil allows for a continuous measurement of the up and down motion of the front probe 102 based on known relations between magnetic field strength and distance. By obtaining these calculations, the motion of the probe 102 can then be included in the estimate of liver motion.

It will thus be appreciated that precise knowledge about probe orientation and vertical motion allows compensation for the effects of both front probe motion and abdominal surface shape.

In development of embodiments of the invention, some potential safety issues were addressed.

Magnetic field: The electromagnet on the patient's back generates a weak magnetic field, suitably at a frequency of 33 kHz, that decays with the inverse cube of the distance. In all directions, the field strength is below 27 µT at distances of more than 15 mm from the cylindrical magnet centerline. For example, 27 µT is the recommended maximum magnetic field strength for continuous whole-body exposure to the public at frequencies between 3 kHz and 10 MHz. This means that a few milliliters of skin and subcutaneous tissues close to the back sensor will be exposed to field strengths above 27 µT, but always below 100 µT which is the corresponding limit for continuous occupational whole-body exposure.

New Acceleration and Magnetic Sensor Devices in the Front Probe 102 and the Acceleration Sensor Device 128 in the Rear Probe:

The accelerometers 121, 128 and the magnetic pickup coil 122 that have been added to the probes 102, 104 are passive devices without any energy emissions. They therefore do not have any potential for harming the patient.

Physical Pressure Sores on the Dorsal Side of the Patient:

The rear sensor probe 104 might have a potential for creating pressure sores. This has been considered during the design of the sensor. In one embodiment, the probe 104 is suitably encapsulated in a biocompatible soft silicone rubber, and has, e.g., a circular 5 cm diameter flat contact surface for contact with a patient's skin or a surface in the range of 5 to 100 $cm^2$, without sharp edges and with a tapered shape towards its circumference. A suitable attachment location is the back flank of a patient which is a soft tissue region between the rib cage and the pelvis, contributing to an even mechanical pressure distribution. In one embodiment, the attachment to the skin is by using one of the several attachment options used for the front probe, such as a double-sided silicone rubber tape. If the body of the fourth material or the fifth material is tacky, the rear probe may be attached to the dorsal side of the human body via one of these tacky materials.

In order to prevent pressure sores, the skin in and around the sensor attachment area may be carefully inspected during daily re-attachments of the rear probe, and also during routine nursing visits to the patient. The occurrence of skin irritation may be recorded as an adverse event, and the patient in such a situation may be excluded from further participation.

Electrical Safety:

Both probes 102, 104 are fully and hermetically encapsulated, suitably in electrically insulating material, such as silicone rubber with an electrical insulation of 20 kV/mm. In an embodiment, the shortest distance from an electrical conductor inside the probe to the surface is at least 1 mm. At least the bodies of the first and the fourth materials exhibit such electrical insulation properties.

In some embodiments, the device is suitably powered from a medical grade external power supply delivering 12 VDC. The highest voltage found inside the device is preferably not more than 18 to 24 VDC.

Example Embodiment: Motion Compensation

A simplified method of motion compensation based on accelerometer readings of the gravity vector in combination with magnetic range measurements will now be discussed. It is assumed, for the sake of a simplified presentation, that the sensor probe 102 motion is substantially along a direction perpendicular to the plane of the mattress on which the human body of the patient rests.

Rear (Aux) Sensor Probe 104 Orientation

Calculation of the rear sensor probe orientation (e.g., the probe 104 located on the dorsal side of the patient) may be expressed as a rotation matrix relative to the global coordinate frame, and calculation of derived parameters:
  Sine and cosine of mattress tilt angle (a); and
  Unit vectors describing:
    Direction from rear probe 104 to front probe 102. This is also the expected motion direction of the front probe 102,
    The orientation of the electromagnet 129, and
    Direction of expected liver motion 145, a positive direction being towards the patient's head.

Front Sensor Probe Orientation

Calculation of the front probe 102 orientation, with derived parameters, are based on the inputs of the accelerometer 121 readings and tilt of the mattress from the rear (aux) probe 104.

Based on the user instructions about how to orient the front probe and the rear probe, outputs are:
  Unit vectors describing:
    Ultrasound beam direction 143
    Magnet pick-up orientation 149

Distance from Rear Probe to Front Probe

The distance is calculated from the magnetic pick-up signal, the direction from the electromagnet 129 to the pick-up 122, and the orientations of the electromagnet 129 and the pick-up signal 122. This calculation also utilizes a single calibration value (k) determined during production of the system.

Motion Compensation

The distance 148 between the rear probe and the front probe is decomposed along the sound beam direction 143 and differentiated to give incremental motion. This is added to the incremental motion detected by the Doppler system in the same time interval. The summed motion is then corrected for the instantaneous cosine of the angle between the sound beam and the liver motion direction. Displacement is then calculated by integration.

General Aspects

All accelerometer readings are converted to conform with a coordinate system where the axis directions are:
  X: Towards patient's head,
  Y: Towards patient's left arm side, and
  Z: Downwards.

Assuming that the IMUs (inertial measurement units) of the three-axis accelerometers are mounted at integer multiples of 90°, coordinate system conversion be done by a combination of permutations and sign reversals.

All coordinates and rotations in formulas and illustrations are given in the global stationary coordinate system unless otherwise specified.

For the calculations below, where the accelerometer readings only are used for determination of angular orientations, they do not need to be converted from raw binary format to metric units, as long as the numeric format is signed.

Rear Probe 104 Orientation:

Accelerometer readings are: $a_{Ax}$, $a_{Ay}$, and $a_{Az}$ (signed, arbitrary units)

It is assumed that the electrical cord points straight outwards to the patients' right side, and that the cord, ferrite rod and accelerometer y-axis are parallel.

The orientation of the probe 104 may be described by a sequence of two rotations:
  1) An initial rotation of ρ around the global x-axis to account for the local transverse curvature of the patients back (roll); and
  2) A rotation of a around the global Y-axis to account for the tilt of the bed (pitch).

Figure 29:
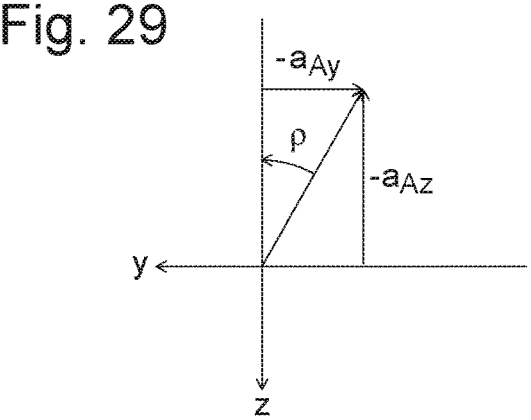
FIG. 29 illustrates an example graph showing first rotation (p) seen from the positive x-axis, according to embodiments of the present disclosure.

The rotations are derived by considering the probe and its measured gravity vector as a stiff body, and performing rotations that aligns the gravity vector with the negative global z-axis. The first rotation aligns the gravity vector with the x-z plane. For example, FIG. 29 illustrates an example graph showing a first rotation (p) seen from the positive x-axis, which can be calculated as follows:

$$\sin(\rho) = \frac{-a_{Ay}}{\sqrt{a_{Ay}^2 + a_{Az}^2}} \text{ and} \qquad \text{Eqn. (1)}$$

$$\cos(\rho) = \frac{-a_{Az}}{\sqrt{a_{Ay}^2 + a_{Az}^2}} \qquad \text{Eqn. (2)}$$

And the corresponding rotation matrix is:

$$R_{A1} = \begin{bmatrix} 1 & 0 & 0 \\ 0 & \cos(\rho) & -\sin(\rho) \\ 0 & \sin(\rho) & \cos(\rho) \end{bmatrix} \qquad \text{Eqn. (3)}$$

Figure 30:
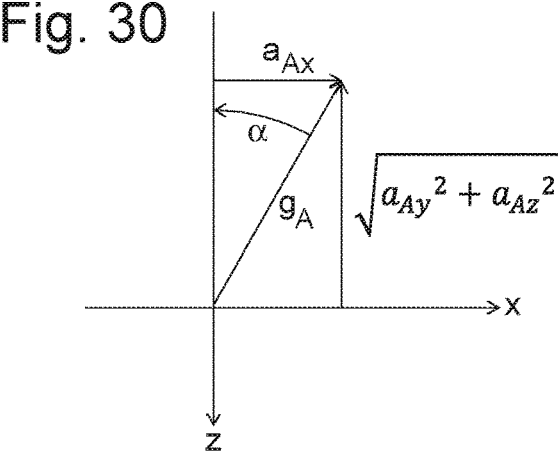
FIG. 30 illustrates an example graph showing orientation of the gravity vector prior to a second rotation as seen from the positive y-axis, according to embodiments of the present disclosure.

FIG. 30 shows an example of orientation of the gravity vector prior to the second rotation as seen from the positive y-axis. The second rotation is calculated as follows:

$$g_A = \sqrt{a_{Ax}^2 + a_{Ay}^2 + a_{Az}^2} \qquad \text{Eqn. (4)}$$

$$\sin(\alpha) = \frac{a_{Ax}}{g_A} \text{ and} \qquad \text{Eqn. (5)}$$

$$\cos(\alpha) = \frac{\sqrt{a_{Ay}^2 + a_{Az}^2}}{g_A} \qquad \text{Eqn. (6)}$$

Note that $\sin(\alpha)$ and $\cos(\alpha)$ are normally utilized for calculation of front probe 102 orientation. The angle $\alpha$ itself might not need to be evaluated.

The corresponding rotation matrix is:

$$R_{A2} = \begin{bmatrix} \cos(\alpha) & 0 & \sin(\alpha) \\ 0 & 1 & 0 \\ -\sin(\alpha) & 0 & \cos(\alpha) \end{bmatrix} \qquad \text{Eqn. (7)}$$

The full rotation is thus:

$$R_{aux} = R_{A2} R_{A1} \qquad \text{Eqn. (8)}$$

The unit vector orientation of the electromagnet in the second magnetic field unit 129 of the rear probe 104 is:

$$\hat{v}_{magnet} = R_{aux} \begin{bmatrix} 0 \\ 1 \\ 0 \end{bmatrix} \qquad \text{Eqn. (9)}$$

The unit vector direction of liver motion expressed in the global coordinate system is:

$$\hat{v}_{liver} = R_{A2} \begin{bmatrix} 1 \\ 0 \\ 0 \end{bmatrix} = \begin{bmatrix} \cos(\alpha) \\ 0 \\ -\sin(\alpha) \end{bmatrix} \qquad \text{Eqn. (10)}$$

The unit vector from the rear electromagnet 129 to the front sensor pickup 122 is:

$$\hat{v}_{mm} = R_{A2} \begin{bmatrix} 0 \\ 0 \\ -1 \end{bmatrix} = \begin{bmatrix} -\sin(\alpha) \\ 0 \\ -\cos(\alpha) \end{bmatrix} \qquad \text{Eqn. (11)}$$

Front Probe 102 Orientation:

Accelerometer readings are: $a_{Px}$, $a_{Py}$, and $a_{Pz}$

Bed tilt angle is: $\alpha$ (from back sensor, expressed as $\sin(\alpha)$ and $\cos(\alpha)$).

A sequence of rotations that positions the probe 102 in a manner that makes the measured acceleration vertical and upwards, and assures that the probe 102 x-axis and the body centerline are in the same plane are:

1) A rotation of $\varphi$ around y to account for the local taper of the body surface;
2) A rotation of $\theta$ around x to account for the position of the probe 102 in the right flank; and
3) A final rotation of a (bed tilt) around y.

The calculations are derived by finding the sequence of rotations of a stiff body consisting of the probe 102 and its associated measured gravity vector that aligns the measured gravity vector with the global negative z-axis (upwards).

Figure 31:
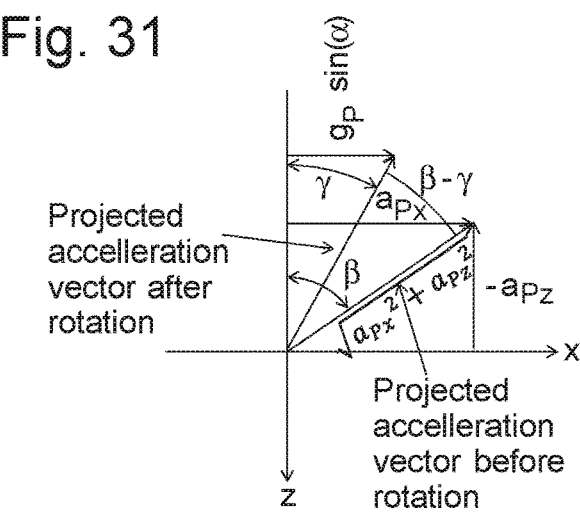
FIG. 31 illustrates an example graph showing probe coordinates and measured acceleration seen from the positive y-axis, according to embodiments of the present disclosure.

For rotation (1), the initial condition is presented by Equations 12-19 below and illustrated by FIG. 31. For example, FIG. 31 illustrates probe coordinates and measured acceleration seen from the positive y-axis. The first rotation is around the y-axis with an angle of $\varphi=\beta-\gamma$ which causes the measured acceleration vector to point such that a remaining distance to the global y-z plane is $g_P \sin(\alpha)$.

The equations include:

$$g_P = \sqrt{a_{Px}^2 + a_{Py}^2 + a_{Pz}^2} \qquad \text{Eqn. (12)}$$

$$\sin(\beta) = \frac{a_{Px}}{\sqrt{a_{Px}^2 + a_{Pz}^2}} \text{ and} \qquad \text{Eqn. (13)}$$

$$\cos(\beta) = \frac{-a_{Pz}}{\sqrt{a_{Px}^2 + a_{Pz}^2}} \qquad \text{Eqn. (14)}$$

$$\sin(\gamma) = \frac{g_P \sin(\alpha)}{\sqrt{a_{Px}^2 + a_{Pz}^2}} \text{ and} \qquad \text{Eqn. (15)}$$

$$\cos(\gamma) = \sqrt{1 - \sin^2(\gamma)} \qquad \text{Eqn. (16)}$$

It should be noted that the following condition is to be fulfilled for valid calculations:

$$|g \sin(\alpha)| \leq \sqrt{a_{Px}^2 + a_{Pz}^2}$$

In some embodiments, user errors in probe 102 placement (e.g., improper orientation) might cause this condition. If this happens, an error message may be given, and the session may be re-started.

The rotation angle $\gamma$ has the following properties:

$$\cos(\phi) = \cos(\beta-\gamma) = \cos(\beta)\cos(\gamma) + \sin(\beta) + \sin(\gamma) \qquad \text{Eqn. (17)}$$

$$\sin(\phi) = \sin(\beta-\gamma) = \sin(\beta)\cos(\gamma) - \cos(\beta)\sin(\gamma) \qquad \text{Eqn. (18)}$$

The rotation matrix is thus:

$$R_{P1} = \begin{bmatrix} \cos(\phi) & 0 & \sin(\phi) \\ 0 & 1 & 0 \\ -\sin(\phi) & 0 & \cos(\phi) \end{bmatrix} \qquad \text{Eqn. (19)}$$

Figure 32:
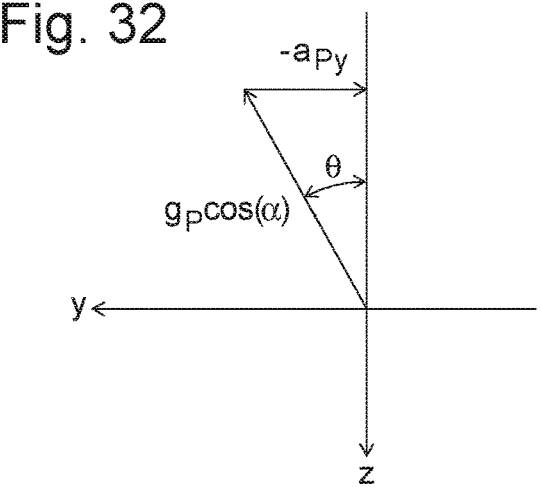
FIG. 32 illustrates an example graph showing a situation after the first rotation seen from the global positive x-axis, according to embodiments of the present disclosure.

For rotation (2), the situation is illustrated by FIG. 32 and related Equations 20-22. For example, FIG. 32 shows the situation after rotation (1) seen from the global positive x-axis. The next rotation (2) around the global x-axis may bring the acceleration vector into the global x-z plane. The equations include:

$$\sin(\theta) = \frac{-a_{Py}}{g_P \cos(\alpha)} \text{ and} \qquad \text{Eqn. (20)}$$

$$\cos(\theta) = \sqrt{1 - \sin^2(\theta)} \qquad \text{Eqn. (21)}$$

The rotation matrix is thus:

$$R_{P2} = \begin{bmatrix} 1 & 0 & 0 \\ 0 & \cos(\theta) & -\sin(\theta) \\ 0 & \sin(\theta) & \cos(\theta) \end{bmatrix} \qquad \text{Eqn. (22)}$$

Figure 33:
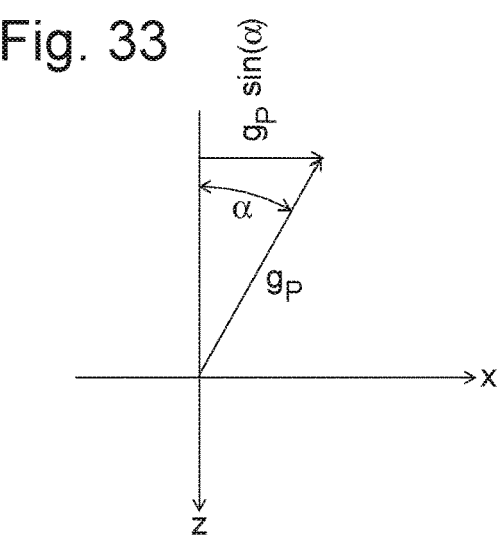
FIG. 33 illustrates direction of the measured acceleration vector after the second rotation, according to embodiments of the present disclosure.

FIG. 33 shows the direction of the measured acceleration vector after rotation (2). The last rotation around the global y-axis will align the vector with the negative z-axis of the global coordinate system.

For rotation (3), the rotation matrix:

$$R_{P3} = \begin{bmatrix} \cos(\alpha) & 0 & \sin(\alpha) \\ 0 & 1 & 0 \\ -\sin(\alpha) & 0 & \cos(\alpha) \end{bmatrix} \qquad \text{Eqn. (23)}$$

As a note, $R_{P3}$ may be the same as $R_{A2}$, from Eqn. (7) and might not need to be recalculated.

The full rotation is then calculated as follows:

$$R_{front} = R_{P3} R_{P2} R_{P1} \qquad \text{Eqn. (24)}$$

The ultrasound beam direction (45° downwards) is:

$$\hat{v}_{beam} = R_{front} \begin{bmatrix} \cos(45°) \\ 0 \\ \sin(45°) \end{bmatrix} \qquad \text{Eqn. (25)}$$

In some embodiments, these trigonometric functions are preferably pre-calculated.

The orientation of the magnet pickup 122 (angled, in one embodiment, at 26° rotation around the probe x-axis) is:

$$\hat{v}_{pickup} = R_{front} \begin{bmatrix} 0 \\ \cos(26°) \\ \sin(26°) \end{bmatrix} \quad \text{Eqn. (26)}$$

In some embodiments, these trigonometric functions are also preferably pre-calculated.

Magnet Distance Measurements 148:

The inputs to the calculation of distance are:

$N_{cal}$: The signal reading during calibration. It is assumed that the emitting magnets in the second magnetic field unit 129 and the receiving magnets in the first magnetic field unit 122 are oriented parallel with each other on a flat surface and orthogonal to the distance between their centerlines when the system is calibrated;

$S_{cal}$: The distance between the magnets 122, 129 during calibration;

$N_{meas}$: The signal reading during measurements;

$v_{mm}$: Unit vector from magnet 129 to pickup 122;

$v_{magnet}$: Unit vector giving the orientation of the electromagnet 129; and $v_{pickup}$: Unit vector giving the orientation of the magnet pickup 122 in the front probe 102.

The formula for the external magnetic field from a dipole is calculated as follows:

$$B = \frac{|\mu|}{S^3}[3(\hat{v}_{magnet} \cdot \hat{v}_{mm}) \cdot \hat{v}_{mm} - \hat{v}_{magnet}] \quad \text{Eqn. (27)}$$

S is the distance from the dipole along the direction given by $v_{mm}$, and $|\mu|$ is the magnitude of the magnet dipole moment. Note that multiplications of vectors with vectors are scalar products. A circumflex (^) indicates a unit vector.

The received signal ($N_{meas}$) from the pickup coil 122 will be the component of the field that is parallel with the pickup 122 according to the following equation:

$$N_{meas} = \frac{k}{S^3}[3(\hat{v}_{magnet} \cdot \hat{v}_{mm}) \cdot \hat{v}_{mm} - \hat{v}_{magnet}] \cdot \hat{v}_{pickup} \quad \text{Eqn. (28)}$$

Here, k is a constant that combines $|\mu|$, the physical properties of the coils, amplification, ADC properties, demodulation and signal averaging. The constant k is determined by a calibration procedure.

Solving Equation 28 with respect to S gives the following distance ($S_{mag}$):

$$S_{mag} = \sqrt[3]{\frac{k}{N_{meas}}[3(\hat{v}_{magnet} \cdot \hat{v}_{mm}) \cdot \hat{v}_{mm} - \hat{v}_{magnet}] \cdot \hat{v}_{pickup}} \quad \text{Eqn. (29)}$$

Calibration:

K is determined during calibration. Assuming that the ferrite rods are located at a distance of $S_{cal}$ from each other, and oriented as indicated by FIG. 34, then solving Equation 28 provides:

$$k = \frac{N_{cal} S_{cal}^3}{[3(\hat{v}_{magnet} \cdot \hat{v}_{mm}) \cdot \hat{v}_{mm} - \hat{v}_{magnet}] \cdot \hat{v}_{pickup}} \quad \text{Eqn. (30)}$$

Figure 34:
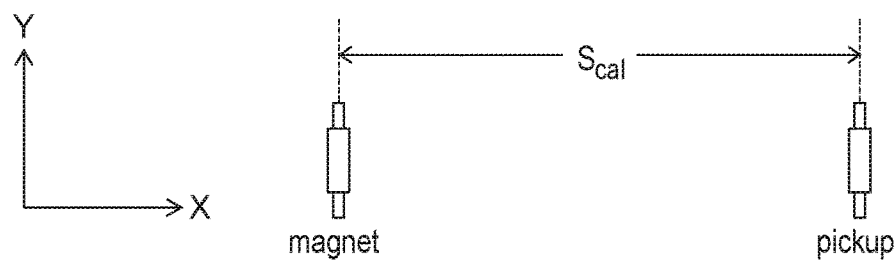
FIG. 34 illustrates a calibration setup, according to embodiments of the present disclosure.

Inserting values for vectors $v_{magnet}$, $v_{pickup}$ and $v_{mm}$ that describes the geometry of the calibration setup in FIG. 34 results in:

$$k = \frac{N_{cal} S_{cal}^3}{\left[\left(3\begin{bmatrix}0\\1\\0\end{bmatrix} \cdot \begin{bmatrix}1\\0\\0\end{bmatrix}\right) \cdot \begin{bmatrix}1\\0\\0\end{bmatrix} - \begin{bmatrix}0\\1\\0\end{bmatrix}\right] \cdot \begin{bmatrix}0\\1\\0\end{bmatrix}} = -N_{cal} S_{cal}^3 \quad \text{Eqn. (31)}$$

Note that the measurement units for $S_{cal}$ are the same as the units for $S_{mag}$. If calibration is performed with the pickup rotated 26° (placing the assembled probe on a flat surface), then k instead becomes:

$$k = \frac{N_{cal} S_{cal}^3}{\left[\left(3\begin{bmatrix}0\\1\\0\end{bmatrix} \cdot \begin{bmatrix}1\\0\\0\end{bmatrix}\right) \cdot \begin{bmatrix}1\\0\\0\end{bmatrix} - \begin{bmatrix}0\\1\\0\end{bmatrix}\right] \cdot \begin{bmatrix}0\\\cos(26°)\\\sin(26°)\end{bmatrix}} = -\frac{N_{cal} S_{cal}^3}{\cos(26°)} \quad \text{Eqn. (32)}$$

Practical Implementation of Calibrated Distance Measurements:

The constant k is determined during production of each system of probes according to Equation 31 and is stored in non-volatile memory. In this example embodiment described herein, a practical value for $S_{cal}$ is 0.25 m.

Motion Compensation

The motion compensation method described herein compensates for continuous variations in beam orientation, bed angle, and abdominal surface motion. It assumes that the abdominal surface moves in a direction ($v_{mm}$) perpendicular to the mattress.

Data from the different sensors in the probes are preconditioned to have identical sample rates and delays, and the sign of the ultrasound-based range measurements ($S_{ultr}$) is such that motion of the liver towards the patients head is positive. The letter delta ($\Delta$) signifies differences between consecutive samples.

The incremental motion of the liver between two successive sample points when corrected for the angle between the magnet range measurement and the ultrasound beam, and for angle between the ultrasound beam and liver motion is:

$$\Delta S_{liver} = \frac{\Delta S_{mag}(\hat{v}_{mm} \cdot \hat{v}_{beam}) + \Delta S_{ultr}}{\hat{v}_{beam} \cdot \hat{v}_{liver}} \quad \text{Eqn. (33)}$$

It may be noted that if $v_{beam}$ and $v_{liver}$ are close to perpendicular to each other, (e.g. as ($|\hat{v}_{beam} \cdot \hat{v}_{liver}| < 0.2$)), an error message or warning may be issued since measurements then will be very angle-dependent and inaccurate.

The instantaneous velocity of the liver 144 is found as:

$$\text{Velocity} = \frac{\Delta S_{liver}}{\Delta t}, \quad \text{Eqn. (34)}$$

where $\Delta t$ is the time between samples.

The position of the liver is found by summation of $\Delta S_{liver}$.

Thus, it may be summarized that in order to compensate for movement detection errors related to an internal structure of one of the liver, the spleen, and a kidney of the human, it is useful to exploit a 3-axis accelerometer unit in the front and rear probes to measure tilt based on direction of gravity, and using the magnetic field unit in the front probe to measure up and down motion of the probe with the assistance of the second magnetic field unit which emits a magnetic field. By adding the rear probe to be located on the dorsal side of the human, that probe having the second accelerometer unit, it is also possible to measure tilt angle of a bed on which the patient rests, assuming that the liver moves along the same direction as the bed surface. It is then possible to compute an angle between liver motion and an ultrasound beam instead of assuming that the beam has a stationary value of, e.g., 45°. The present disclosure thereby offers the possibility to compute contribution of up and down motion to the ultrasound Doppler signal provided, and thereby compensate for the related signal errors.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A respiration detection system comprising:
 a first probe comprising:
  an ultrasonic transducer stationary located within the first probe and having a transceiving face oriented at an acute angle relative to a front plane of the first probe, wherein the ultrasonic transducer is configured to produce an ultrasound beam at the transceiving face for transmission into an internal structure inside a body of a patient,
  a first accelerometer unit, and
  a first magnetic field unit, wherein the ultrasonic transducer, the first accelerometer unit, and the first magnetic field unit are stationary located in the first probe; and
 a second probe comprising:
  a second accelerometer unit, and
  a second magnetic field unit, wherein the second accelerometer unit and the second magnetic field unit are stationary located in the second probe;
 wherein the ultrasonic transducer, the first and second accelerometer units, and the first and second magnetic field units are coupled to a signal processor,
 wherein the first probe is configured to be placed on a front side of the body of the patient,
 wherein the second probe is configured to be placed on a dorsal side of the body of the patient, and
 wherein combination of the first and second accelerometer units and the first and second magnetic field units are configured to produce output signals that are a function of spatial positional movement and orientation of the ultrasonic transducer upon respiration by the patient.

2. The respiration detection system of claim 1, wherein the first and second accelerometer units each comprise at least two accelerometers.

3. The respiration detection system of claim 1, wherein the first accelerometer unit includes a three-axis accelerometer device.

4. The respiration detection system of claim 1, wherein the spatial positional movement and the orientation are related to at least one of heave, roll, pitch and yaw type movements.

5. The respiration detection system of claim 1,
 wherein the ultrasonic transducer is located in the first probe by means of a body of a first material comprising ultrasound non-sonolucent material which extends towards the front plane of the first probe,
 wherein the body of the first material surrounds a recess extending from the transceiving face towards the front plane of the first probe,
 wherein a first body part of a second material comprising ultrasound sonolucent material is located in the recess at and in front of the transceiving face of the ultrasonic transducer towards the front plane of the first probe, and
 wherein a second body part of the second material is applied onto a front surface of the body of the first material and made integrally engaged therewith, the first and second body parts being integral.

6. The respiration detection system of claim 5, wherein the ultrasonic transducer is engaged within a socket-like member positioned within the recess, and wherein the socket-like member is formed of ultrasound non-sonolucent material.

7. The respiration detection system of claim 5, wherein a front surface of a body of the second material comprises an inherent tacky property, an attachment face for an adhesive member or a double-sided adhesive tape, or an engagement face for a tacky layer of a body of a third material.

8. The respiration detection system of claim 7, wherein the adhesive member or the double-sided adhesive tape is ultrasound sonolucent at least at a region faced by the transceiving face of the ultrasonic transducer.

9. The respiration detection system of claim 7, wherein the tacky layer of the body of the third material is ultrasound sonolucent.

10. The respiration detection system of claim 7, wherein the first accelerometer unit and the first magnetic field unit are stationary located in the first probe by use of the first material.

11. The respiration detection system of claim 7, wherein the second accelerometer unit and the second magnetic field unit are stationary located in the second probe by means of a body of a fourth material.

12. The respiration detection system of claim 11, wherein a front surface of the body of the fourth material comprises a tacky property, an attachment face for an adhesive member or a double-sided tacky tape, or an engagement face for a tacky layer of a body of a fifth material.

13. The respiration detection system of claim 12, wherein at least one of the first, second, third, fourth and fifth materials is of a silicone type.

14. The respiration detection system of claim 1, wherein a first one of the first magnetic field unit and the second magnetic field unit comprises a magnetic field sensor device, and wherein the other one of the first magnetic field unit and the second magnetic field unit comprises an electromagnet device configured to generate a magnetic field to be detected by the magnetic field sensor device, and wherein the magnetic field is related to a distance between the first and second probes.

15. The respiration detection system of claim 14, wherein the signal processor controls intensity, frequency and duration of the generated magnetic field.

16. The respiration detection system of claim 14, wherein the magnetic field sensor device is a magnetic pickup coil.

17. The respiration detection system of claim 1, wherein the first probe is configured to be placed on the front side of the body of the patient at a position vertically above the second probe positioned on the dorsal side of the body of the patient when the body of the patient is supine.

18. The respiration detection system of claim 1, wherein the first probe is configured to be placed on the front side of the body of the patient at a position aligned with the second probe on the dorsal side of the body of the patient.

19. The respiration detection system of claim 1, wherein the second accelerometer unit provides for measurement of tilt angles of a surface supporting the dorsal side of the body of the patient.

20. The respiration detection system of claim 1, wherein a surface of the second probe configured to contact a dorsal skin area of the body of the patient comprises a biocompatible material, and wherein a skin contact area of the surface of the second probe is in the range of 5 cm$^2$ to 100 cm$^2$.

21. The respiration detection system of claim 1, wherein the signal processor is configured to calculate, based on inputs from the first and second accelerometer units and from the first magnetic field unit interacting with the second magnetic field unit, movement and orientation of an abdominal wall of the patient in relation to direction of expected motion of an internal structure inside the body of the patient, the movement and orientation of the abdominal wall being related to respiration parameters associated with respiratory muscles of the patient.

22. The respiration detection system of claim 21, wherein the internal structure is one of a liver, spleen, or kidney of the patient.

23. The respiration detection system of claim 21, wherein the expected motion of the internal structure is a function of thoracic diaphragm movement in the body of the patient.

24. The respiration detection system of claim 1, wherein:
the ultrasonic transducer in the first probe is configured to receive ultrasound echo signals from the internal structure;
the second magnetic field unit is configured to generate a magnetic field transmitted to and detected by the first magnetic field unit;
the signal processor is configured to calculate:
an orientation of the first accelerometer unit relative to a fixed coordinate frame using derived parameters from the first accelerometer unit,
the derived parameters as unit vectors representing an orientation of the ultrasound beam and an orientation of the first magnetic field unit,
an orientation of the second accelerometer unit relative to a fixed coordinate frame using further derived parameters from the second accelerometer unit,
the further derived parameters including body back support tilt angle ($\alpha$) and unit vectors representative of a spatial direction from the second magnetic field unit to the first magnetic field unit,
an orientation of the second magnetic field unit,
an expected direction of motion of the internal structure during exhalation, and
any varying distance between the first and second magnetic field units based on the detection of the magnetic field; and
the signal processor is further configured to process results from the calculated orientations of the first and second accelerometer units, derived parameters from the first and second accelerometer units, and the varying distance to generate correction parameters to compensate for measurement errors in received ultrasound echo signals.

25. The respiration detection system of claim 24, wherein to generate the correction parameters, the signal processor is further configured to:
decompose a vector representing the distance between the first magnetic field unit and the second magnetic field unit along the direction of the ultrasound beam;
differentiate in time the decomposed vector representing the distance to yield incremental motion values;
add the incremental motion values to incremental Doppler effect motion values as detected by use of ultrasound echo signals from the internal structure in at least a same time interval;
correct the added motion values for an instantaneous cosine value of an angle between the ultrasound beam and direction of motion of the internal structure; and
sum the corrected and added motion values to obtain internal structure position variations describing corrected respiratory parameters.

26. A respiration detection system comprising:
a first probe comprising:
an ultrasonic transducer stationary located within the first probe and having a transceiving face oriented at an acute angle relative to a front plane of the first probe, wherein the ultrasonic transducer is configured to produce an ultrasound beam at the transceiving face for transmission into an internal structure inside a body of a patient,
a first accelerometer unit, and
a first magnetic field unit, wherein the ultrasonic transducer, the first accelerometer unit, and the first magnetic field unit are stationary located in the first probe; and
a second probe comprising:
a second accelerometer unit, and
a second magnetic field unit, wherein the second accelerometer unit and the second magnetic field unit are stationary located in the second probe;
wherein the ultrasonic transducer, the first and second accelerometer units, and the first and second magnetic field units are coupled to a signal processor, wherein the first probe is configured to be placed on a front side of the body of the patient, wherein the second probe is configured to be placed on a dorsal side of the body of the patient, and wherein the signal processor is configured to calculate, based on inputs from the first and second accelerometer units and from the first magnetic field unit interacting with the second magnetic field unit, movement and orientation of an abdominal wall of the patient in relation to direction of expected motion of an internal structure inside the body of the patient, the movement and orientation of the abdominal wall being related to respiration parameters associated with respiratory muscles of the patient.

27. The respiration detection system of claim 26, wherein the internal structure is one of a liver, spleen, or kidney of the patient.

28. The respiration detection system of claim 26, wherein the expected motion of the internal structure is a function of thoracic diaphragm movement in the body of the patient.

29. The respiration detection system of claim 26, wherein:

the ultrasonic transducer in the first probe is configured to receive ultrasound echo signals from the internal structure;

the second magnetic field unit is configured to generate a magnetic field transmitted to and detected by the first magnetic field unit;

the signal processor is configured to calculate:
   an orientation of the first accelerometer unit relative to a fixed coordinate frame using derived parameters from the first accelerometer unit,
   the derived parameters as unit vectors representing an orientation of the ultrasound beam and an orientation of the first magnetic field unit,
   an orientation of the second accelerometer unit relative to a fixed coordinate frame using further derived parameters from the second accelerometer unit,
   the further derived parameters including body back support tilt angle ($\alpha$) and unit vectors representative of a spatial direction from the second magnetic field unit to the first magnetic field unit,
   an orientation of the second magnetic field unit,
   an expected direction of motion of the internal structure during exhalation, and
   any varying distance between the first and second magnetic field units based on the detection of the magnetic field; and the signal processor is further configured to process results from the calculated orientations of the first and second accelerometer units, derived parameters from the first and second accelerometer units, and the varying distance to generate correction parameters to compensate for measurement errors in received ultrasound echo signals.

30. The respiration detection system of claim 29, wherein to generate the correction parameters, the signal processor is further configured to:

decompose a vector representing the distance between the first magnetic field unit and the second magnetic field unit along the direction of the ultrasound beam;

differentiate in time the decomposed vector representing the distance to yield incremental motion values;

add the incremental motion values to incremental Doppler effect motion values as detected by use of ultrasound echo signals from the internal structure in at least a same time interval;

correct the added motion values for an instantaneous cosine value of an angle between the ultrasound beam and direction of motion of the internal structure; and sum the corrected and added motion values to obtain internal structure position variations describing corrected respiratory parameters.

* * * * *

UNITED STATES PATENT AND TRADEMARK OFFICE
CERTIFICATE OF CORRECTION

PATENT NO. : 10,398,351 B1  
APPLICATION NO. : 16/216632  
DATED : September 3, 2019  
INVENTOR(S) : Eriksen et al.

Page 1 of 1

It is certified that error appears in the above-identified patent and that said Letters Patent is hereby corrected as shown below:

On the Title Page

Column 1, Item (72), in "Inventors", Line 4, delete "Olso" and insert -- Oslo --, therefor.

Signed and Sealed this  
Twenty-fifth Day of February, 2020

Andrei Iancu  
*Director of the United States Patent and Trademark Office*